United States Patent
Hioki et al.

(10) Patent No.: US 11,608,405 B2
(45) Date of Patent: Mar. 21, 2023

(54) POLYCARBONATE POLYOL AND POLYURETHANE

(71) Applicant: Mitsubishi Chemical Corporation, Chiyoda-ku (JP)

(72) Inventors: Yuta Hioki, Chiyoda-ku (JP); Yoshikazu Kanamori, Chiyoda-ku (JP); Kazunao Kusano, Chiyoda-ku (JP); Kazuki Wakabayashi, Chiyoda-ku (JP); Ryo Yamashita, Chiyoda-ku (JP); Takayuki Yamanaka, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 347 days.

(21) Appl. No.: 16/448,007

(22) Filed: Jun. 21, 2019

(65) Prior Publication Data
US 2019/0315908 A1  Oct. 17, 2019

Related U.S. Application Data

(63) Continuation of application No. PCT/JP2017/045947, filed on Dec. 21, 2017.

(30) Foreign Application Priority Data

Dec. 22, 2016  (JP) ............... JP2016-249483
Jul. 24, 2017  (JP) ............... JP2017-142831

(51) Int. Cl.
| | |
|---|---|
| C08G 18/44 | (2006.01) |
| C07C 31/20 | (2006.01) |
| C07C 31/22 | (2006.01) |
| C08G 64/02 | (2006.01) |
| C08L 75/04 | (2006.01) |
| C08G 18/66 | (2006.01) |
| C08G 18/32 | (2006.01) |
| C08G 18/76 | (2006.01) |

(52) U.S. Cl.
CPC .......... *C08G 18/44* (2013.01); *C07C 31/20* (2013.01); *C07C 31/225* (2013.01); *C08G 18/3206* (2013.01); *C08G 18/6637* (2013.01); *C08G 64/02* (2013.01); *C08L 75/04* (2013.01); *C08G 18/7671* (2013.01)

(58) Field of Classification Search
CPC .... C08G 18/44; C08G 64/02; C08G 18/7671; C08G 18/3206; C08G 18/6637; C07C 31/20; C07C 31/225; C08L 75/04
See application file for complete search history.

(56) References Cited

U.S. PATENT DOCUMENTS

| | | |
|---|---|---|
| 5,143,997 A | 9/1992 | Endo et al. |
| 5,952,450 A | 9/1999 | Ishihara et al. |
| 2007/0083002 A1 | 4/2007 | Schafheutle et al. |
| 2008/0021154 A1 | 1/2008 | Haider et al. |
| 2013/0066044 A1 | 3/2013 | Allen et al. |
| 2015/0291724 A1 | 10/2015 | Kusano et al. |
| 2016/0177027 A1 | 6/2016 | Lee et al. |

FOREIGN PATENT DOCUMENTS

| | | |
|---|---|---|
| CN | 104884499 A | 9/2015 |
| CN | 105473636 A | 4/2016 |
| FR | 1 155 285 A | 4/1958 |
| JP | 3-220233 | 9/1991 |
| JP | 11-116668 | 4/1999 |
| JP | 3684567 | 8/2005 |
| JP | 2006-299020 | 11/2006 |
| JP | 2008-530253 | 8/2008 |
| JP | 2009-544801 | 12/2009 |
| JP | 2012-502143 | 1/2012 |
| JP | 5111159 | 12/2012 |

(Continued)

OTHER PUBLICATIONS

International Search Report dated Feb. 27, 2018 in PCT/JP2017/045947, filed on Dec. 21, 2017.
English translation of the International Preliminary Report on Patentability and Written Opinion of the International Searching Authority dated Jul. 4, 2019 in PCT/JP2017/045947, 6 pages.
Combined Chinese Office Action and Search Report dated Dec. 30, 2020 in Chinese Patent Application No. 201780079184.7 (with English translation), 13 pages.
Extended European Search Report dated Sep. 10, 2019 in European Patent Application No. 17884134.2, 6 pages.

(Continued)

*Primary Examiner* — Rabon A Sergent
(74) *Attorney, Agent, or Firm* — Oblon, McClelland, Maier & Neustadt, L.L.P.

(57) ABSTRACT

Provided is a polycarbonate polyol used as a raw material of a polyurethane that has an excellent balance of flexibility, mechanical strength and solvent resistance. The polycarbonate polyol includes structural units derived from a polyhydric alcohol and has a hydroxyl value of 20 to 450 mg KOH/g. The polyhydric alcohol includes: a diol (A) containing not less than 70% by weight of a specific oxyalkylene glycol (A1); and a trihydric to hexahydric branched alcohol (B) having 3 to 12 carbon atoms. In the polycarbonate polyol, structural units derived from the branched alcohol (B) is contained in an amount of 0.005 to 5.0% by mole in the structural units derived from the polyhydric alcohol. A ratio of a structural unit (X1) represented by the following Formula (X1) in the structural units derived from the branched alcohol (B) is not higher than 50% by mole.

(A1)

(X1)

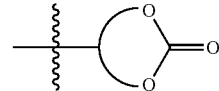

10 Claims, No Drawings

(56) References Cited

FOREIGN PATENT DOCUMENTS

| JP | 5448627 | 3/2014 |
|----|---------|--------|
| JP | 2016-527376 | 9/2016 |

OTHER PUBLICATIONS

Combined Taiwanese Office Action and Search Report dated May 13, 2021 in Taiwanese Patent Application No. 106145338 (with unedited computer generated English translation), 7 pages.

Decision of Rejection dated Dec. 6, 2021 issued in corresponding Taiwanese application No. 106145338 with its machine translation.

Combined Chinese Office Action and Search Report dated Aug. 16, 2021 in Chinese Patent Application No. 201780079184.7 (with English translation), 13 pages.

POLYCARBONATE POLYOL AND POLYURETHANE

CROSS-REFERENCE TO RELATED APPLICATION

This is a continuation of International Application PCT/JP2017/045947, filed on Dec. 21, 2017, and designated the U.S., and claims priority from Japanese Patent Application 2016-249483 which was filed on Dec. 22, 2016, and Japanese Patent Application 2017-142831 which was filed on Jul. 24, 2017, the entire contents of which are incorporated herein by reference.

TECHNICAL FIELD

The present invention relates: a polycarbonate polyol used as a raw material of a polyurethane that has an excellent balance of flexibility, mechanical strength and solvent resistance; and a polyurethane using the polycarbonate polyol.

BACKGROUND ART

Polycarbonate diols are used as raw materials for soft segments of polyurethanes and thermoplastic elastomers as well as in paints, adhesives and the like, and such polycarbonate diols are widely used as high durability-imparting raw materials that are excellent in, for example, heat resistance, weather resistance and hydrolysis resistance that are otherwise regarded as drawbacks of polyether polyols and polyester polyols.

Among polycarbonate diols, those synthesized from 1,6-hexanediol are widely commercially available at present; however, these polycarbonate diols have high crystallinity and thus present a problem that, when processed into a polyurethane, the soft segment thereof is highly cohesive and the polyurethane exhibits poor flexibility, elongation, bending or elasticity recovery particularly at low temperatures; therefore, the use of such polycarbonate diols has been limited. Furthermore, it has been pointed out that an artificial leather produced using the resulting polyurethane as a raw material has a hard feel and poor "texture" as compared to a natural leather.

In order to solve these problems, polycarbonate diols which are produced using an oxyalkylene glycol as a raw material and have excellent flexibility and solvent resistance have been proposed, and Patent Documents 1 and 2 disclose polycarbonate diols using diethylene glycol. Further, Patent Document 3 discloses a polycarbonate diol obtained by copolymerizing 1,6-hexanediol and triethylene glycol.

However, the polycarbonate diols of Patent Documents 1 and 2 are each constituted solely by an oxyalkylene glycol and thus do not have sufficient mechanical strength and, in Patent Document 3, since an oxyalkylene glycol component is introduced with a half amount or more of other diol component, there is a problem that the chemical resistance and flexibility intrinsic to a polycarbonate diol obtained by using an oxyalkylene glycol as a raw material are impaired.

Meanwhile, in order to improve the hardness, the mechanical strength and the solvent resistance, polycarbonate polyols obtained by copolymerizing a diol with a tri- or higher hydric alcohol have been proposed. For example, Patent Document 4 describes that a polycarbonate polyol having a high hardness was obtained using a combination of a tri- or higher hydric alcohol, a monool and a diol. Patent Document 5 discloses a polycarbonate polyol which is obtained using 1,6-hexanediol and trimethylolpropane and has a high density and excellent mechanical strength.

RELATED ART DOCUMENTS

Patent Documents

Patent Document 1: Japanese Patent No. 5448627
Patent Document 2: Japanese Patent No. 5111159
Patent Document 3: Japanese Patent No. 3684567
Patent Document 4: Japanese Laid-open Patent Application (Kokai) No. 2006-299020
Patent Document 5: Japanese Laid-open Patent Application (Kokai) No. H03-220233

SUMMARY OF THE INVENTION

Problems to be Solved by the Invention

As described above, a number of proposals have been previously made with regard to polycarbonate polyols obtained by copolymerizing a diol and a tri- or higher hydric alcohol; however, in the synthesis of a polyurethane demanded to be flexible and strong at the same time, although the type, the introduction amount and the cross-linking amount of a polyhydric alcohol used as raw material of a polycarbonate polyol greatly affect the performance of the resulting polyurethane, these properties of the polyhydric alcohol have not been sufficiently examined, and a further improvement is currently demanded for the resulting polyurethane.

That is, when the crosslinking amount is overly increased by the introduction of a polyhydric alcohol, the flexibility is impaired due to gelation and, when the resulting polyurethane is used for an artificial leather, the leather has poor texture. Meanwhile, an excessively small crosslinking amount leads to insufficient mechanical strength. Particularly, when a polyhydric alcohol is introduced to an oxyalkylene glycol having a large amount of hydrogen bond, the resulting polyurethane has a structure whose soft segments readily aggregate. Therefore, there are problems that gelation is likely to occur during the polyurethane synthesis and that the flexibility of the resulting polyurethane is thus likely to be reduced, making the polyurethane brittle.

An object of the present invention is to provide: a polycarbonate polyol used as a raw material of a polyurethane that has an excellent balance of flexibility, mechanical strength and solvent resistance, which could not be achieved in prior art; and a polyurethane using the polycarbonate polyol.

Means for Solving the Problems

The present inventors intensively studied to solve the above-described problems and consequently discovered that the problems can be solved by using a specific oxyalkylene glycol and a specific branched alcohol in a polyhydric alcohol used as a raw material of a polycarbonate polyol and controlling the ratio of structural units derived from the branched alcohol in the polycarbonate polyol and the ratio of cyclic polycarbonate terminal groups in the structural units derived from the branched alcohol.

That is, the gist of the present invention is as follows.

[1] A polycarbonate polyol including structural units derived from a polyhydric alcohol and having a hydroxyl value of 20 mg KOH/g to 450 mg KOH/g, wherein the polyhydric alcohol contains a diol (A) and a trihydric to hexahydric branched alcohol (B) having 3 to 12 carbon atoms, the diol (A) contains an oxyalkylene glycol (A1) represented by the following Formula (A1) at a ratio of 70% by weight or higher, a ratio of structural units derived from the branched alcohol (B) is 0.005% by mole to 5.0% by mole with respect to a total amount of the structural units derived from the polyhydric alcohol, and a ratio of a structural unit (X1) represented by the following Formula (X1) in the structural units derived from the branched alcohol (B) is not higher than 50% by mole:

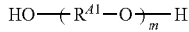
(A1)

(wherein, m represents an integer of 2 to 4; $R^{41}$ represents a carbon chain optionally containing a branch having 2 to 5 carbon atoms; and m $R^{41}$s contained in Formula (A1) are optionally the same or different)

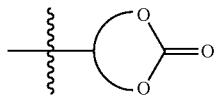
(X1)

[2] The polycarbonate polyol according to [1], wherein the branched alcohol (B) contains a partial structure (B2) represented by the following Formula (B2), and the structural unit (X1) in the polycarbonate polyol, which is derived from the partial structure (B2), is a structural unit (X2) represented by the following Formula (X2):

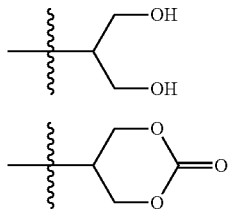
(B2)

(X2)

[3] The polycarbonate polyol according to [1] or [2], wherein the branched alcohol (B) is a trihydric alcohol.

[4] The polycarbonate polyol according to [3], wherein the trihydric alcohol is trimethylolpropane.

[5] The polycarbonate polyol according to any one of [1] to [4], wherein the oxyalkylene glycol (A1) contains at least one selected from the group consisting of diethylene glycol, triethylene glycol, tetraethylene glycol, and dipropylene glycol.

[6] The polycarbonate polyol according to [5], wherein the oxyalkylene glycol (A1) contains diethylene glycol and/or triethylene glycol.

[7] The polycarbonate polyol according to [6], wherein a total content ratio of diethylene glycol and triethylene glycol in the diol (A) is not less than 70% by weight.

[8] The polycarbonate polyol according to [6] or [7], wherein a weight ratio of diethylene glycol and triethylene glycol in the oxyalkylene glycol (A1) is 10:90 to 90:10 (diethylene glycol:triethylene glycol).

[9] A polyurethane obtainable using a polycarbonate polyol, wherein
the polycarbonate polyol includes structural units derived from a polyhydric alcohol and has a hydroxyl value of 20 mg KOH/g to 450 mg KOH/g,
the polyhydric alcohol contains a diol (A) and a trihydric to hexahydric branched alcohol (B) having 3 to 12 carbon atoms,
the diol (A) contains an oxyalkylene glycol (A1) represented by the following Formula (A1) and a content ratio of the oxyalkylene glycol (A1) in the diol (A) is 70% by weight or higher,
a ratio of structural units derived from the branched alcohol (B) in the polycarbonate polyol is 0.005% by mole to 5.0% by mole with respect to a total amount of the structural units derived from the polyhydric alcohol in the polycarbonate polyol, and
a ratio of a structural unit (X1) represented by the following Formula (X1) in the structural units derived from the branched alcohol (B) is not higher than 50% by mole:

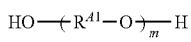
(A1)

(wherein, m represents an integer of 2 to 4; $R^{41}$ represents a carbon chain optionally containing a branch having 2 to 5 carbon atoms; and m $R^{41}$s contained in Formula (A1) are optionally the same or different)

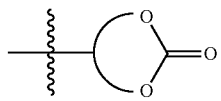
(X1)

[10] The polyurethane according to [9], which is obtainable using the polycarbonate polyol, an organic polyisocyanate compound, and a chain extender.

[11] A polyurethane obtainable using the polycarbonate polyol according to any one of [1] to [8].

Effects of the Invention

A polyurethane which as high flexibility and high mechanical strength as well as excellent solvent resistance can be provided by polymerizing the polycarbonate polyol of the present invention with an isocyanate or the like. Further, the problem of gelation during the polyurethane synthesis is suppressed, so that excellent stable productivity can be attained.

A polyurethane produced using the polycarbonate polyol of the present invention is characterized by showing good reactivity in urethane polymerization and having excellent balance of flexibility, mechanical strength and solvent resistance; therefore, it is suitable for applications such as elastic fibers, synthetic or artificial leathers, paints and highly functional elastomers and thus extremely effective industrially.

MODE FOR CARRYING OUT THE INVENTION

The present invention will now be described in detail; however, the present invention is not restricted to the following descriptions and can be modified arbitrarily within a range that does not depart from the gist of the present invention.

It is noted here that, in the present specification, those ranges that are expressed with "to" before and after numerical or physical property values each denote a range that includes the respective numerical or physical property values. Further, in the present specification, "% by mass", "ppm by mass" and "parts by mass" have the same meanings as "% by weight", "ppm by weight" and "parts by weight", respectively. Moreover, a simple term "ppm" used herein indicates "ppm by weight".

[1. Polycarbonate Polyol]

The polycarbonate polyol according to one aspect of the present invention is a polycarbonate polyol which is obtained by a polycondensation reaction using a polyhydric alcohol and a carbonate compound as raw materials and has a hydroxyl value of 20 mg KOH/g to 450 mg KOH/g, the polycarbonate polyol being characterized in that: the polyhydric alcohol contains a diol (A) and a trihydric to hexahydric branched alcohol (B) having 3 to 12 carbon atoms; the diol (A) contains an oxyalkylene glycol (A1) represented by the following Formula (A1) and the content ratio of the oxyalkylene glycol (A1) in the diol (A) is 70% by weight or higher; the ratio of structural units derived from the branched alcohol (B) in the polycarbonate polyol is 0.005% by mole to 5.0% by mole with respect to a total amount of structural units derived from the polyhydric alcohol in the polycarbonate polyol; and the ratio of a structural unit (X1) represented by the following Formula (X1) in the structural units derived from the branched alcohol (B) is not higher than 50% by mole.

(A1)

(wherein, m represents an integer of 2 to 4; $R^{41}$ represents a carbon chain optionally containing a branch having 2 to 5 carbon atoms; and m $R^{41}$s contained in Formula (A1) are optionally the same or different).

(X1)

<1-1. Characteristics of Structure Derived from Raw Material Polyhydric Alcohol>
<1-1-1. Oxyalkylene Glycol (A1) and Content Ratio Thereof>

The polycarbonate polyol according to one aspect of the present invention contains not less than 70% by weight of an oxyalkylene glycol (A1) represented by the following Formula (A1) in a raw material diol (A) and, by incorporating the oxyalkylene glycol (A1) at such a ratio, excellent flexibility and solvent resistance (hereinafter, the term "solvent resistance" encompasses chemical resistance) are attained. From the standpoints of the flexibility and the solvent resistance, the content ratio of the oxyalkylene glycol (A1)

in the diol (A) is preferably 80 to 100% by weight, more preferably 90 to 100% by weight.

(A1)

(wherein, m represents an integer of 2 to 4; $R^{41}$ represents a carbon chain optionally containing a branch having 2 to 5 carbon atoms; and m $R^{41}$s contained in Formula (A1) are optionally the same or different)

In a polycarbonate polyol obtainable using the oxyalkylene glycol (A1) at such a ratio, the ratio of a structural unit derived from the oxyalkylene glycol (A1) is usually 70% by weight or higher, preferably 80 to 100% by weight, more preferably 90 to 100% by weight, with respect to a total amount of structural units derived from the diol (A).

The oxyalkylene glycol (A1) is not particularly restricted as long as it is represented by the above-described Formula (A1); however, from the standpoints of the flexibility and the solvent resistance, the number of carbon atoms of $R^{41}$ in Formula (A1) is preferably 2 or 3, more preferably 2. Specific examples of the carbon chain optionally containing a branch having 2 to 5 carbon atoms, which is represented by $R^{41}$, include linear or branched alkylene groups having 2 to 5 carbon atoms.

Specific preferred examples of the oxyalkylene glycol (A1) include diethylene glycol, triethylene glycol, tetraethylene glycol, and dipropylene glycol. These oxyalkylene glycols (A1) may be used singly, or in combination of two or more thereof.

As the oxyalkylene glycol (A1), it is particularly preferred to use diethylene glycol and/or triethylene glycol and, from the standpoints of the flexibility and the chemical resistance, the total content ratio of diethylene glycol and triethylene glycol in the raw material diol (A) is preferably 70% by weight or higher, particularly preferably 80 to 100% by weight, especially preferably 90 to 100% by weight.

Particularly, the use of a combination of diethylene glycol and triethylene glycol as the oxyalkylene glycol (A1) is a preferred mode in the present invention since this inhibits aggregation due to hydrogen bonding by disturbing the regularity of structural units in the polycarbonate polyol chain and the flexibility is thereby improved. In this case, diethylene glycol and triethylene glycol are used at a weight ratio (diethylene glycol:triethylene glycol) of preferably 10:90 to 90:10, particularly preferably 30:70 to 70:30, more preferably 40:60 to 60:40.

In cases where the raw material diol (A) of the polycarbonate polyol contains a diol other than the oxyalkylene glycol (A1) represented by Formula (A1), examples of such other diol include linear diols having 2 to 20 carbon atoms, such as ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, and 1,12-dodecanediol; branched diols having 4 to 20 carbon atoms, such as 2-methyl-1,3-propanediol, 2-ethyl-1,3-propanediol, 2,2-dimethyl-1,3-propanediol, 2-ethyl-2-butyl-1,3-propanediol, 2,2-diethyl-1,3-propanediol, 3-methyl-1,5-pentanediol, 3,3-dimethyl-1,5-pentanediol, 2,2,4,4-tetramethyl-1,5-pentanediol, and 2-ethyl-1,6- hexanediol; cyclic diols having 6 to 20 carbon atoms, such as 1,3-cyclohexanediol, 1,4-cyclohexanediol, 1,4-cyclohexanedimethanol, 4,4-dicyclohexyldimethylmethanediol, 2,2'-bis(4-hydroxycyclohexyl)propane, 4,4'-isopropylidenedicyclohexanol, and norbornane-2,3-dimethanol; and cyclic diols having a hetero atom in a ring, such as isosorbide, 3,4-dihydroxytetrahydrofuran, 3,9-bis(1,1-dimethyl-2-hydroxyethyl)-2,4,8,10-tetraoxaspiro[5.5]undecane (cas number: 1455-42-1), and 2-(5-ethyl-5-hydroxymethyl-1,3-dioxane-2-yl)-2-methylpropan-1-ol (cas number: 59802-10-7).

These other diols may be used singly, or in combination of two or more thereof; however, as described above, in order to obtain the effect of improving the flexibility and the solvent resistance, which effect is attributed to the use of the oxyalkylene glycol (A1), the content of other diol(s) in the diol (A) is 30% by weight or less, preferably 20% by weight or less, more preferably 10% by weight or less.

<1-1-2. Branched Alcohol (B) and Content Ratio Thereof>

In the polycarbonate polyol according to one aspect of the present invention, the diol (A) containing the oxyalkylene glycol (A1) at the above-described ratio and a branched alcohol (B) are used as raw material polyhydric alcohols, and the ratio of structural units derived from the branched alcohol (B) in the polycarbonate polyol is controlled to be 0.005% by mole to 5.0% by mole with respect to a total amount of structural units derived from the raw material polyhydric alcohols in the polycarbonate polyol, whereby excellent mechanical strength can be attained because of crosslinked structured introduced by the branched alcohol (B) without deterioration of the flexibility and the solvent resistance that are provided by the oxyalkylene glycol (A1).

From the standpoint of satisfying the flexibility and the solvent resistance as well as the mechanical strength, the ratio of the structural units derived from the branched alcohol (B) in the structural units derived from the raw material polyhydric alcohols contained in the polycarbonate polyol is preferably 0.005 to 5.0% by mole, more preferably 0.05 to 3.0% by mole, still more preferably 0.5 to 2.0% by mole.

In order to control the ratio of the structural units derived from the branched alcohol (B) in the structural units derived from the raw material polyhydric alcohols contained in the polycarbonate polyol to be in the above-described range, the molar content ratio of the branched alcohol (B) in the polyhydric alcohols used as raw materials of the polycarbonate polyol may be set in the above-described range.

In other words, generally, the ratio of each polyhydric alcohol in the raw material polyhydric alcohols is substantially the same as the ratio of the structural unit derived from each polyhydric alcohol with respect to the total amount of the structural units derived from the raw material polyhydric alcohols in the resulting polycarbonate polyol.

In cases where the branched alcohol (B) is used as a raw material polyhydric alcohol of a polycarbonate polyol, a linear structural unit, a branched structural unit, and a structural unit (X1), which is a terminal group of a cyclic carbonate structure represented by the following Formula (X1), are introduced as structural units derived from the branched alcohol in the resulting polycarbonate polyol.

(X1)

For example, when the branched alcohol (B) has at least two methylol groups and contains a partial structure (B2) represented by the following Formula (B2), a terminal group of a cyclic carbonate structure of a structural unit (X2) represented by the following Formula (X2), which is derived from the partial structure (B2), is introduced into the resulting polycarbonate polyol.

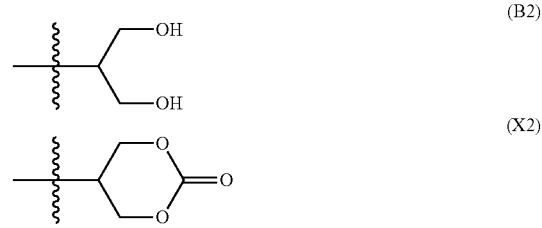

(B2)

(X2)

Further, when a polycarbonate polyol is produced using, for example, the oxyalkylene glycol (A1) as the diol (A), trimethylolpropane as the branched alcohol (B) and a carbonate compound, a polycarbonate polyol having the structural units shown below (a structural unit derived from the oxyalkylene glycol (A1), (1) a branched structural unit derived from trimethylolpropane, (2) a chain structural unit derived from trimethylolpropane, and (3) a structural unit (X2) which is a terminal group of a cyclic carbonate structure derived from trimethylolpropane) is obtained.

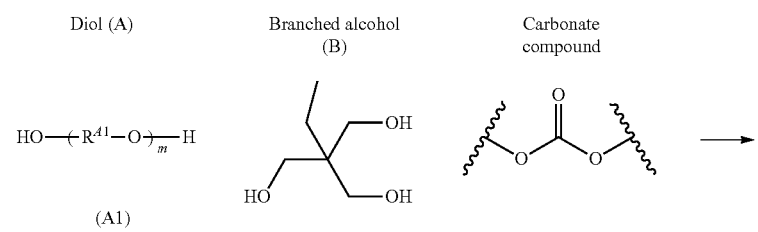

Diol (A)  Branched alcohol (B)  Carbonate compound (A1)

| Structural unit derived from (A) | Structural units derived from (B) |
|---|---|
| 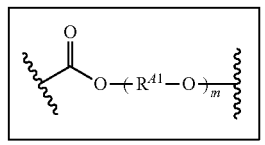 | 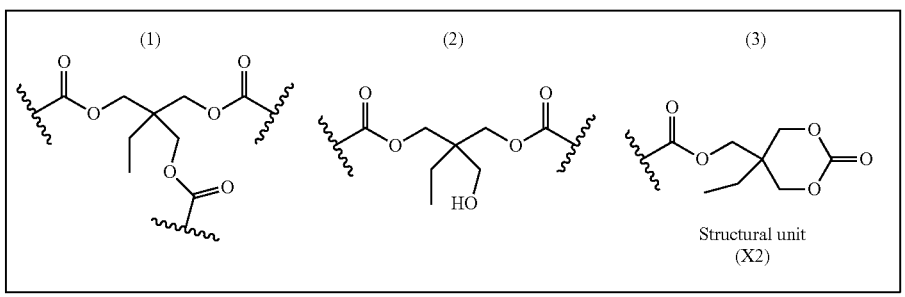 |

Cyclic carbonate terminal groups, such as the above-described structural units (X1) and (X2), cannot react with a polyisocyanate in a urethanization reaction and thus contribute to neither of an increase in the molecular weight of the resulting polyurethane nor an improvement in the mechanical strength attributed thereto. Therefore, the amount of such cyclic carbonate terminal groups in the polycarbonate polyol is preferably small.

In the polycarbonate polyol according to one aspect of the present invention, the ratio of the cyclic carbonate terminal group of the structural unit (X1), which is not involved in the urethanization reaction, in the structural units derived from the branched alcohol (B) is low at 50% by mole or less; therefore, the polycarbonate polyol can yield a polyurethane having excellent mechanical strength. Since the lower the ratio of the cyclic carbonate terminal group of the structural unit (X1) in the polycarbonate polyol, the more preferred it is from the standpoint of the mechanical strength of the resulting polyurethane, this ratio is preferably 40% by mole or less. However, in order to produce a polycarbonate polyol containing the structural unit (X1) at a low ratio, it is necessary to extend the reaction time, which is not preferred from the productivity standpoint, and the resulting polycarbonate polyol may be colored due to an extended reaction time; therefore, the ratio of the structural unit (X1) in the structural units derived from the branched alcohol (B) is preferably 1% by mole or higher, more preferably 5% by mole or higher, still more preferably 10% by mole or higher, particularly preferably 20% by mole or higher, most preferably 25% by mole or higher.

In the polycarbonate polyol, the content ratios of the structural units derived from the polyhydric alcohols, the structural units derived from the branched alcohol (B) and the structural unit (X1) can be determined by an NMR analysis, and the details of the analysis method are as described below in the section of Examples.

In the polycarbonate polyol according to one aspect of the present invention, in order to control the content ratios of the structural units derived from the branched alcohol (B) and the structural unit (X1) in the above-described respective preferred ranges, with regard to the structural units derived from the branched alcohol (B), the branched alcohol (B) may be used in the raw material polyhydric alcohols such that a polycarbonate polyol having the above-described content ratio of the structural units derived from the branched alcohol (B) can be obtained. The structural unit (X1) is reduced by the progress of reaction with the polyhydric alcohols and the carbonate compound. Specifically, the content ratio of the structural unit (X1) can be controlled in the above-described range by modifying, for example, the reaction time, the reaction temperature, the stirring rate, the reactor and/or the stirring device, by adding the polyhydric alcohols, the carbonate compound and a transesterification catalyst at a later time, or by selecting the types of the polyhydric alcohols, the carbonate compound and the transesterification catalyst. In other words, by extending the reaction time, the content ratio of the structural unit (X1) can be reduced. Moreover, when the raw material polyhydric alcohols and the carbonate compound are reduced in the latter half of the reaction, the sites of the reaction with the structural unit (X1) can be increased by further adding the polyhydric alcohols. Similarly, the transesterification rate can be accelerated by adding the carbonate compound, and the reaction activity can be increased by adding an appropriate transesterification catalyst. In addition, by selecting polyhydric alcohols, carbonate compound and transesterification catalyst of appropriate types, their reactivity with the structural unit (X1) can be improved.

Examples of the trihydric to hexahydric branched alcohol (B) having 3 to 12 carbon atoms that is contained in the raw material polyhydric alcohols of the polycarbonate polyol according to one aspect of the present invention include glycerol, trimethylolmethane, trimethylolethane, trimethylolpropane, trimethylolbutane, 1,2,4-butanetriol, 1,2,3-hexanetriol, 1,2,4-hexanetriol, tris(hydroxymethyl)amine, tris(hydroxyethyl)amine, tris(hydroxypropyl)amine, pentaerythritol, diglycerol, triglycerol, polyglycerol, bis(trimethylolpropane), tris(hydroxymethyl)isocyanurate, tris(hydroxyethyl)isocyanurate, saccharides such as glucose, and saccharide derivatives such as sorbitol. In the polycarbonate polyol, structural units derived from these branched alcohols (B) may be contained singly, or two or more thereof may be contained in combination. In other words, as the raw material polyhydric alcohols of the polycarbonate polyol, the above-described branched alcohols (B) may be used singly, or in combination of two or more thereof.

Thereamong, from the standpoint of the efficiency of introducing crosslinked structures, branched alcohols containing at least some of, preferably all of, their hydroxy groups in the form of methylol groups are particularly preferred, and the smaller the number of the carbon atoms thereof, the more preferred it is. In other words, methylol groups have a structure containing hydroxy groups via a methylene group and are thus highly reactive. Further, when branched alcohols are added at the same number of moles, the one having a smaller number of carbon atoms can further increase the crosslinking density. However, when the number of the carbon atoms of the branched alcohol (B) is excessively small, the reactivity of the hydroxy groups is poor due to steric hindrance, and this makes the crosslinking unlikely to proceed. In addition, an excessively high density of crosslinking points may facilitate gelation. Accordingly, as the branched alcohol (B), a methylol group-containing trihydric to hexahydric branched alcohol having 3 to 12 carbon atoms is preferred, and the number of carbon atoms is more preferably 4 to 10. Specifically, the branched alcohol (B) is preferably a trihydric alcohol such as glycerol, trimethylolpropane, trimethylolethane or trimethylolmethane, a tetrahydric alcohol such as pentaerythritol or ditrimethylolpropane, or a hexahydric alcohol such as dipentaerythritol, particularly preferably a trihydric alcohol that is capable of forming a structural unit having an appropriate crosslinking density to inhibit gelation, most preferably trimethylolpropane that contains three highly reactive methylol groups and is industrially readily available and inexpensive.

<1-1-3. Preferred Raw Material Polyhydric Alcohols>

In the polycarbonate polyol according to one aspect of the present invention, from the standpoints of the flexibility, the solvent resistance and the mechanical strength, it is particularly preferred to use the diol (A) containing diethylene glycol and/or triethylene glycol and the branched alcohol (B) containing trimethylolpropane as raw material polyhydric alcohols, and it is especially preferred to use diethylene glycol, triethylene glycol and trimethylolpropane at ratios of 30 to 70% by mole, 30 to 70% by mole and 0.005 to 5% by mole, respectively, with respect to a total of 100% by mole of these components.

It is noted here that the raw material polyhydric alcohols of the polycarbonate polyol according to one aspect of the present invention may also contain a polyhydric alcohol other than the above-described diol (A) and branched alcohol (B), such as a tri- or higher hydric linear alcohol or a tri- or higher hydric cyclic alcohol; however, from the standpoint of effectively attaining the above-described effects attributed to the use of the diol (A) and branched alcohol (B), the content of the polyhydric alcohol other than the diol (A) and branched alcohol (B) in the raw material polyhydric alcohols is preferably 30% by weight or less, particularly preferably 20% by weight or less, more preferably 10% by weight or less, and it is most preferred that the raw material polyhydric alcohols do not contain any such alcohol.

<1-2. Carbonate Compound>

The carbonate compound used in the production of the polycarbonate polyol according to one aspect of the present invention is not restricted as long as the effects of the present invention are not impaired, and examples of the carbonate compound include dialkyl carbonates, diaryl carbonates, and alkylene carbonates.

Thereamong, the use of a diaryl carbonate is advantageous in that it allows the reaction to proceed quickly and that the diaryl carbonate reacts with low-reactivity polyhydric alcohols and structural units in the polycarbonate polyols, and this can consequently reduce the ratio of the above-described structural unit (X1) in the structural units derived from the branched alcohol (B).

Specific examples of dialkyl carbonates, diaryl carbonates and alkylene carbonates that can be used for producing the polycarbonate polyol according to one aspect of the present invention are as follows.

Examples of the dialkyl carbonates include dimethyl carbonate, diethyl carbonate, dibutyl carbonate, dicyclohexyl carbonate, diisobutyl carbonate, ethyl-n-butyl carbonate, and ethylisobutyl carbonate, among which dimethyl carbonate and diethyl carbonate are preferred.

Examples of the diaryl carbonates include diphenyl carbonate, ditolyl carbonate, bis(chlorophenyl) carbonate, and di-m-cresyl carbonate, among which diphenyl carbonate is preferred.

Examples of the alkylene carbonates include ethylene carbonate, trimethylene carbonate, tetramethylene carbonate, 1,2-propylene carbonate, 1,2-butylene carbonate, 1,3-butylene carbonate, 2,3-butylene carbonate, 1,2-pentylene carbonate, 1,3-pentylene carbonate, 1,4-pentylene carbonate, 1,5-pentylene carbonate, 2,3-pentylene carbonate, 2,4-pentylene carbonate, and neopentyl carbonate, among which ethylene carbonate is preferred.

These carbonates may be used singly, or in combination of two or more thereof.

Among the above-described carbonates, diaryl carbonates are preferred since they are highly reactive and efficient in terms of industrial production and, among such diaryl carbonates, diphenyl carbonate that can be easily and inexpensively obtained as an industrial material is more preferred.

In the production of the polycarbonate polyol according to one aspect of the present invention, the amount of the carbonate compound to be used is not particularly restricted; however, usually, in terms of molar ratio with respect to a total of 1 mol of the raw material polyhydric alcohols, the lower limit of the amount is preferably 0.35, more preferably 0.50, still more preferably 0.60, while the upper limit is preferably 1.00, more preferably 0.98, still more preferably 0.97. When the amount of the carbonate compound is greater than the upper limit, there are cases where the ratio of non-hydroxy terminal groups in the resulting polycarbonate polyol is increased or the molecular weight of the polycarbonate polyol is not controlled in a prescribed range, whereas when the amount of the carbonate compound is less than the lower limit, there are cases where polymerization does not proceed to a prescribed molecular weight, or a large amount of the structural unit (X1) remains in the structural units derived from the branched alcohol (B) and crosslinking thus does not proceed sufficiently.

<1-3. Transesterification Catalyst>

The polycarbonate polyol according to one aspect of the present invention can be produced by polycondensation of the above-described polyhydric alcohols and carbonate compound through a transesterification reaction.

In the production of the polycarbonate polyol according to one aspect of the present invention, a transesterification catalyst (hereinafter, may be referred to as "catalyst") is usually used to accelerate polymerization. As the transesterification catalyst, any compound that is generally considered to be capable of catalyzing transesterification can be used with no restriction.

Examples of the transesterification catalyst include compounds of Group 1 metals of long-form periodic table (hereinafter, simply referred to as "periodic table"), such as lithium, sodium, potassium, rubidium, and cesium; compounds of periodic table Group 2 metals, such as magnesium, calcium, strontium, and barium; compounds of periodic table Group 4 metals, such as titanium, zirconium, and hafnium; compounds of periodic table Group 5 metals; compounds of periodic table Group 9 metals, such as cobalt; compounds of periodic table Group 12 metals, such as zinc; compounds of periodic table Group 13 metals, such as aluminum; compounds of periodic table Group 14 metals, such as germanium, tin, and lead; compounds of periodic table Group 15 metals, such as antimony and bismuth; and compounds of lanthanide metals, such as lanthanum, cerium, europium, and ytterbium. Thereamong, from the standpoint of increasing the transesterification reaction rate, compounds of periodic table Group 1 metals, compounds of periodic table Group 2 metals, compounds of periodic table Group 4 metals, compounds of periodic table Group 5 metals, compounds of periodic table Group 9 metals, compounds of periodic table Group 12 metals, compounds of periodic table Group 13 metals, and compounds of periodic table Group 14 metals are preferred, and compounds of periodic table Group 1 metals and compounds of periodic table Group 2 metals are more preferred, and compounds of periodic table Group 2 metals are still more preferred. Among the compounds of periodic table Group 1 metals, compounds of lithium, potassium and sodium are preferred, compounds of lithium and sodium are more preferred, and a compound of sodium is still more preferred. Among the compounds of periodic table Group 2 metals, compounds of magnesium, calcium and barium are preferred, compounds of calcium and magnesium are more preferred, and a compound of magnesium is still more preferred. These metal compounds are mainly used as hydroxides, salts or the like. When the metal compounds are used as salts, examples thereof include halide salts, such as chlorides, bromides, and iodides; carboxylates, such as acetates, formates, and benzoates; sulfonates, such as methanesulfonates, toluenesulfonates, and trifluoromethanesulfonates; phosphorus-containing salts, such as phosphates, hydrogen phosphates, and dihydrogen phosphates; acetylacetonate salts; nitrates; sulfates; and carbonates. These catalyst metals can also be used as alkoxides, such as methoxides and ethoxides.

Among the above-described compounds, the transesterification catalyst is preferably an acetate, nitrate, sulfate, carbonate, phosphate, hydroxide, halide or alkoxide of at least one metal selected from the periodic table Group 2 metals, more preferably an acetate, carbonate or hydroxide of a periodic table Group 2 metal, still more preferably an acetate, carbonate or hydroxide of magnesium or calcium, particularly preferably an acetate of magnesium or calcium, most preferably magnesium acetate.

Further, from the standpoint of allowing, for example, the low-reactivity branched alcohol (B), the structural unit (X1) and a terminal group of an oxyaryl structure derived from the carbonate compound, which are contained in the polycarbonate polyol according to one aspect of the present invention, to react with each other, the transesterification catalyst is preferably a compound of a periodic table Group 1 metal, which is a low-period metal having a low electronegativity and exhibits a high transesterification catalytic action because of strong coordination to the carbonate compound, a compound of a periodic table Group 2 metal, or an acetate, nitrate, sulfate, carbonate, phosphate, hydroxide, halide or alkoxide of a periodic table Group 4 metal. Meanwhile, the raw materials and the oxyalkylene glycol (A1) contained in the polycarbonate polyol structural units are degraded in a strongly acidic or strongly basic condition and, since this causes such problems that the molecular weight is not increased and a hazardous low-molecular-weight compound (1,4-dioxane) and the like are generated as by-products, the transesterification catalyst is preferably a compound of a periodic table Group 2 metal having a moderate basicity. In order to reduce, for example, the low-reactivity branched alcohol (B), the structural unit (X1) and the terminal group of the oxyaryl structure derived from the carbonate compound, the transesterification catalyst is particularly preferably an acetate, carbonate or hydroxide of magnesium or calcium, which maintains high stability even after an extended reaction time, and the transesterification catalyst is most preferably magnesium acetate.

When the above-described catalyst is used and an excessively large amount of the catalyst remains in the resulting polycarbonate polyol, the catalyst may interfere with the reaction or overly facilitate the reaction in the production of a polyurethane using the polycarbonate polyol.

Therefore, when a transesterification catalyst is used, the amount thereof is preferably such an amount that does not affect the performance even if the catalyst remains in the resulting polycarbonate polyol and, with regard to the weight ratio in terms of metal with respect to the weight of all polyhydric alcohols, the upper limit is preferably 500 ppm, more preferably 100 ppm, still more preferably 50 ppm, particularly preferably 10 ppm. Meanwhile, the lower limit is an amount that provides sufficient polymerization activity, which is preferably 0.01 ppm, more preferably 0.1 ppm, still more preferably 1 ppm.

Moreover, when a compound of a periodic table Group 2 metal is used as the catalyst, the total amount of all metal atoms in the compound per 1 mol of all polyhydric alcohols used as raw materials is preferably 5 µmol or greater, more preferably 7 µmol or greater, still more preferably 10 µmol or greater, but preferably 500 µmol or less, more preferably 300 µmol or less, still more preferably 100 µmol or less, particularly preferably 50 µmol or less.

<1-4. Method of Producing Polycarbonate Polyol>

The polycarbonate polyol according to one aspect of the present invention can be produced by using the above-described polyhydric alcohols and the above-described carbonate compound at the above-described respective ratios and transesterifying them in the presence of a transesterification catalyst used as required. A method of producing the polycarbonate polyol will now be described.

A method of charging reaction raw materials is not particularly restricted and can be freely selected from, for example, a method in which the whole amounts of the polyhydric alcohols, the carbonate compound and the transesterification catalyst are charged simultaneously and allowed to react; a method in which, when the carbonate compound is solid, the carbonate compound is charged and heat-melted first, and the polyhydric alcohols and the transesterification catalyst are subsequently added thereto; a method in which, conversely, the polyhydric alcohols are charged and melted first, and the carbonate compound and the transesterification catalyst are subsequently added thereto; and a method in which the polyhydric alcohols are allowed to partially react with the carbonate compound or a chlorocarbonic ester so as to synthesize carbonate diester derivatives of the polyhydric alcohols, and the thus obtained carbonate diester derivatives are subsequently allowed to react with the remaining polyhydric alcohols. In order to control the ratio of the number of molecular chain terminals that are either an alkyloxy group or an aryloxy group to be 5% or lower in the polycarbonate polyol according to one aspect of the present invention, it is also possible to employ a method in which a portion of the polyhydric alcohols to be used is added at the end of the reaction. In this case, the upper limit of the amount of the polyhydric alcohols to be added at the end is usually 20%, preferably 15%, more preferably 10%, of the amount of the polyhydric alcohols to be charged, while the lower limit is usually 0.1%, preferably 0.5%, more preferably 1.0%.

As the reaction temperature during the transesterification, any temperature can be employed as long as it is one at which a practical reaction rate can be attained. This temperature is not particularly restricted; however, it is usually 100° C. or higher, preferably 130° C. or higher, more preferably 150° C. or higher, particularly preferably 160° C.

or higher, but usually 250° C. or lower, preferably 230° C. or lower, more preferably 200° C. or lower, still more preferably 190° C. or lower, particularly preferably 180° C. or lower, most preferably 170° C. or lower.

When the temperature is higher than the above-described upper limit, there may arise problems in quality, such as coloration of the resulting polycarbonate polyol and generation of an ether structure as a by-product due to decarboxylation of carbonate groups or dehydration-condensation between the polyhydric alcohols. In addition, since the polycarbonate polyol according to one aspect of the present invention contains a structural unit derived from the oxyalkylene glycol (A1), at a temperature of higher than the above-described upper limit, there are problems such as cleavage of an oxyalkylene chain and generation of hazardous dioxane due to dehydration-condensation.

The reaction may be performed at normal pressure; however, since the transesterification reaction is an equilibrium reaction, the reaction can be shifted toward a production system by distilling off generated low-boiling-point components to the outside of the system. Accordingly, it is usually preferred to employ a reduced pressure condition in the latter half of the reaction so as to perform the reaction while distilling off the low-boiling-point components. Alternatively, the reaction may be allowed to proceed while distilling off the generated low-boiling-point components by gradually reducing the pressure in the middle of the reaction.

Particularly, the reaction is preferably performed while increasing the degree of reduced pressure in the final period of the reaction since alcohols, phenols and the like that are produced as by-products can thereby be distilled off.

In this case, the reaction pressure at the completion of the reaction is not particularly restricted; however, the upper limit thereof is usually 10 kPa, preferably 5 kPa, more preferably 1 kPa. In order to effectively distill off these low-boiling-point components, the reaction may also be performed while supplying a small amount of an inert gas, such as nitrogen, argon or helium, to the reaction system.

In order to prevent the raw materials from being distilled off in the early stage of the reaction, a reflux condenser may be attached to a reactor and the reaction can be performed while refluxing the carbonate compound and the polyhydric alcohols. In this case, the charged raw materials are not lost and the amount and the ratio of reagents can thus be adjusted accurately, which is preferred.

The reaction time required for the molecular weight to reach a prescribed value is usually 50 hours or shorter, preferably 20 hours or shorter, more preferably 10 hours or shorter and, in the present invention, in order to reduce the ratio of the structural unit (X1), the lower limit of the reaction time is preferably 2 hours or longer.

As described above, when a transesterification catalyst is used in the polymerization reaction, the transesterification catalyst usually remains in the resulting polycarbonate polyol, and this residual transesterification catalyst may make it impossible to control the reaction during polyurethanization. In order to suppress such effect of the residual catalyst, for example, a phosphorus compound may be added in an amount substantially equimolar to the amount of the transesterification catalyst being used. Further, after the addition, by performing a heat treatment as described below, the transesterification catalyst can be efficiently deactivated.

Examples of the phosphorus compound to be used for deactivation of the transesterification catalyst include inorganic phosphoric acids, such as phosphoric acid and phosphorous acid; and organic phosphoric acid esters, such as dibutyl phosphate, tributyl phosphate, trioctyl phosphate, triphenyl phosphate, and triphenyl phosphite.

These phosphorus compounds may be used singly, or in combination of two or more thereof.

The amount of the phosphorus compound to be used is not particularly restricted; however, as described above, it may be substantially equimolar to the amount of the transesterification catalyst used. Specifically, with respect to 1 mol of the transesterification catalyst used, the upper limit is preferably 5 mol, more preferably 2 mol, while the lower limit is preferably 0.6 mol, more preferably 0.8 mol, still more preferably 1.0 mol. If the phosphorus compound is used in a smaller amount, the transesterification catalyst would not be sufficiently deactivated; therefore, when the resulting polycarbonate polyol is used as, for example, a raw material for the production of a polyurethane, the reactivity of the polycarbonate polyol with isocyanate groups cannot be adequately reduced in some cases. Meanwhile, the use of the phosphorus compound in an amount greater than the above-described range may cause coloration in the resulting polycarbonate polyol.

The deactivation of the transesterification catalyst by an addition of the phosphorus compound can be performed at room temperature; however, it is more efficiently performed with a heat treatment. Although the temperature of this heat treatment is not particularly restricted, the upper limit thereof is preferably 180° C., more preferably 150° C., still more preferably 120° C., particularly preferably 100° C., while the lower limit is preferably 50° C., more preferably 60° C., still more preferably 70° C. At a temperature of lower than this lower limit, the deactivation of the transesterification catalyst takes time and is thus not efficient, and the degree of deactivation may be insufficient as well. Meanwhile, at a temperature of higher than the upper limit, the resulting polycarbonate polyol may be colored.

The duration of the reaction with the phosphorus compound is not particularly restricted; however, it is usually 0.1 to 5 hours.

After the polymerization reaction, it is preferred to perform purification for the purpose of removing, from the thus obtained polycarbonate polyol, impurities having an alkyloxy group as a terminal structure and impurities having an aryloxy group as a terminal structure, as well as phenols, the polyhydric alcohols and carbonate compound used as raw materials, the added catalyst and the like. In this purification process, with regard to low-boiling-point compounds, a method of removing them by distillation can be employed. As for a specific method of the distillation, the mode thereof is not particularly restricted and may be any of, for example, vacuum distillation, steam distillation and thin-film distillation, among which thin-film distillation is effective. Further, in order to remove water-soluble impurities, the polycarbonate polyol may be washed with, for example, water, alkaline water, acidic water, or a solution in which a chelating agent is dissolved. In this case, a compound to be dissolved in water can be selected arbitrarily.

The thin-film distillation conditions are not particularly restricted; however, as for the temperature during the thin-film distillation, the upper limit is preferably 250° C., more preferably 200° C., while the lower limit is preferably 120° C., more preferably 150° C.

By setting the lower limit of the temperature during the thin-film distillation at this value, the effect of removing low-boiling-point components is sufficiently attained. Further, by setting the upper limit at 250° C., coloration of the polycarbonate polyol obtained after the thin-film distillation tends to be inhibited.

The upper limit of the pressure during the thin-film distillation is preferably 500 Pa, more preferably 150 Pa, still more preferably 50 Pa. By controlling the pressure during the thin-film distillation to be not higher than this upper limit value, the effect of removing low-boiling-point components tends to be attained sufficiently.

Moreover, as for the temperature at which the polycarbonate polyol is maintained immediately before the thin-film distillation, the upper limit is preferably 250° C., more preferably 150° C., while the lower limit is preferably 80° C., more preferably 120° C.

By controlling the temperature at which the polycarbonate polyol is maintained immediately before the thin-film distillation to be not lower than the above-described lower limit, a reduction in the fluidity of the polycarbonate polyol immediately before the thin-film distillation tends to be inhibited. Meanwhile, by controlling this temperature to be not higher than the above-described upper limit, coloration of the polycarbonate polyol obtained after the thin-film distillation tends to be inhibited.

<1-5. Physical Properties of Polycarbonate Polyol>
<1-5-1. Hydroxyl Value>

The lower limit of the hydroxyl value of the polycarbonate polyol according to one aspect of the present invention is 20 mg KOH/g, preferably 25 mg KOH/g, more preferably 30 mg KOH/g, still more preferably 35 mg KOH/g. Meanwhile, the upper limit of the hydroxyl value of the polycarbonate polyol is 450 mg KOH/g, preferably 230 mg KOH/g, more preferably 150 mg KOH/g, still more preferably 120 mg KOH/g, yet still more preferably 75 mg KOH/g, particularly preferably 60 mg KOH/g, most preferably 45 mg KOH/g. When the hydroxyl value is less than the lower limit, an excessively high viscosity may make the handling of the polycarbonate polyol difficult in polyurethanization, whereas when the hydroxyl value is higher than the upper limit, the physical properties of a polyurethane produced from the polycarbonate polyol, such as flexibility and low-temperature characteristics, may be insufficient.

<1-5-2. Molecular Weight Distribution>

The molecular weight distribution, which is a ratio of the weight-average molecular weight and the number-average molecular weight (Mw/Mn), of the polycarbonate polyol according to one aspect of the present invention is not particularly restricted; however, the lower limit thereof is preferably 1.5, more preferably 1.8, while the upper limit is preferably 3.5, more preferably 3.0. When the molecular weight distribution is higher than this range, a polyurethane produced using this polycarbonate polyol tends to have physical properties of, for example, being hardened and less elongated at low temperatures. When it is intended to produce a polycarbonate polyol having a molecular weight distribution of less than the above-described range, a high-level purification operation such as removal of oligomers may be required.

The weight-average molecular weight and the number-average molecular weight of the polycarbonate polyol are both in terms of polystyrene, and these values can be usually determined by gel permeation chromatography (hereinafter, may be abbreviated as "GPC").

<1-5-3. Molecular Chain Terminals>

The molecular chain terminals of the polycarbonate polyol according to one aspect of the present invention are mainly hydroxy groups. However, in the case of a polycarbonate polyol obtained by a reaction between a polyhydric alcohol and a carbonate compound, non-hydroxy groups may exist as impurities at some of the molecular chain terminals, in addition to the above-described cyclic carbonate terminal group. Specific examples thereof include structures in which molecular chain terminals are an alkyloxy group or an aryloxy group, many of which are derived from the carbonate compound.

For example, when diphenyl carbonate, dimethyl carbonate, diethyl carbonate or ethylene carbonate is used as the carbonate compound, a phenoxy group (PhO—) as an aryloxy group, a methoxy group (MeO—) as an alkyloxy group, an ethoxy group (EtO—) or a hydroxyethoxy group (HOCH$_2$CH$_2$O—) may remain as a molecular chain terminal, respectively (wherein, Ph represents a phenyl group, Me represents a methyl group, and Et represents an ethyl group).

The ratio of the number of terminal groups derived from the carbonate compound at the molecular chain terminals of the polycarbonate polyol is, with respect to the total number of terminal groups, preferably not higher than 5% by mole, more preferably not higher than 3% by mole, more preferably not higher than 1% by mole, still more preferably not higher than 0.5% by mole, particularly preferably not higher than 0.1% by mole.

<1-5-4. Residual Monomers, Etc.>

When a diaryl carbonate such as diphenyl carbonate is used as a raw material, phenols are generated as by-products during the production of the polycarbonate polyol. Phenols are monofunctional compounds and can thus act as inhibitory factors in the production of a polyurethane. In addition, since urethane bonds formed by phenols have a weak bonding force, they are dissociated by heat in the later step or the like, allowing isocyanates and phenols to be regenerated, which potentially causes a problem. Moreover, since phenols are irritating substances, the smaller the amount of phenols remaining in the polycarbonate polyol, the more preferred it is. Specifically, the amount of phenols is, in terms of weight ratio with respect to the polycarbonate polyol, preferably 1,000 ppm by weight or less, more preferably 500 ppm by weight or less, still more preferably 300 ppm by weight or less, particularly preferably 100 ppm by weight or less. In order to reduce the amount of phenols in the polycarbonate polyol, it is effective to control the pressure in the polymerization reaction of the polycarbonate polyol to be a high vacuum of 1 kPa or less in terms of absolute pressure, or to perform thin-film distillation and the like after the polymerization of the polycarbonate polyol.

In the polycarbonate polyol, the carbonate compound used as a raw material in the production may remain. The amount of the carbonate compound remaining in the polycarbonate polyol is not restricted; however, the smaller the amount, the more preferred it is and, in terms of weight ratio with respect to the polycarbonate polyol, the upper limit of the amount is preferably 5% by weight, more preferably 3% by weight, still more preferably 1% by weight. When the amount of the carbonate compound contained in the polycarbonate polyol is excessively large, the carbonate compound may inhibit the reaction in polyurethanization. Meanwhile, the lower limit of the amount is not particularly restricted, and it is preferably 0.1% by weight, more preferably 0.01% by weight, still more preferably 0% by weight.

In the polycarbonate polyol, the polyhydric alcohols in the production may remain as well. The amount of the polyhydric alcohols remaining in the polycarbonate polyol is not restricted; however, the smaller the amount, the more preferred it is and, in terms of weight ratio with respect to the polycarbonate polyol, the amount is preferably 1% by weight or less, more preferably 0.1% by weight or less, still more preferably 0.05% by weight or less. When the amount of the polyhydric alcohols remaining in the polycarbonate polyol is large, the molecular length of soft segment moieties of a polyurethane produced from the polycarbonate polyol may be insufficient, and desired physical properties are thus not attained in some cases.

Further, in the polycarbonate polyol, a cyclic carbonate (cyclic oligomer) generated as a by-product during the production may be contained. For example, when 1,3-propanediol is used, 1,3-dioxan-2-one, a cyclic carbonate formed by two or more molecules thereof, or the like may be generated and contained in the polycarbonate polyol. These compounds can induce a side reaction in the polyurethanization reaction and cause turbidity; therefore, it is preferred to remove them as much as possible by controlling the pressure in the polymerization reaction of the polycarbonate polyol to be a high vacuum of 1 kPa or less in terms of absolute pressure, or by performing thin-film distillation and the like after the synthesis of the polycarbonate polyol. The amount of such a cyclic carbonate contained in the polycarbonate polyol is not restricted; however, in terms of weight ratio with respect to the polycarbonate polyol, the amount is preferably 3% by weight or less, more preferably 1% by weight or less, still more preferably 0.5% by weight or less.

[2. Polyurethane]

A polyurethane can be produced using the polycarbonate polyol according to one aspect of the present invention. The resulting polyurethane is another aspect of the present invention.

With regard to a method of producing the polyurethane of the present invention using polycarbonate polyol according to one aspect of the present invention, polyurethanization reaction conditions known for the polyurethane production are usually employed.

For example, the polyurethane according to one aspect of the present invention can be produced by allowing the polycarbonate polyol according to one aspect of the present invention to react with a polyisocyanate and a chain extender in a range of normal temperature to 200° C.

Alternatively, the polyurethane according to one aspect of the present invention can be produced by first allowing the polycarbonate polyol according to one aspect of the present invention to react with an excess amount of a polyisocyanate so as to produce a prepolymer having isocyanate groups at terminals, and subsequently further increasing the polymerization degree using a chain extender.

<2-1. Polyisocyanate>

Examples of the polyisocyanate used in the polyurethane production along with the polycarbonate polyol include a variety of known aliphatic, alicyclic or aromatic polyisocyanate compounds.

Examples thereof include aliphatic diisocyanates, such as tetramethylene diisocyanate, pentamethylene diisocyanate, hexamethylene diisocyanate, 2,2,4-trimethylhexamethylene diisocyanate, 2,4,4-trimethylhexamethylene diisocyanate, lysine diisocyanate, and dimer diisocyanate obtained by converting carboxyl groups of a dimer acid into isocyanate groups; alicyclic diisocyanates, such as 1,4-cyclohexane diisocyanate, isophorone diisocyanate, 1-methyl-2,4-cyclohexane diisocyanate, 1-methyl-2,6-cyclohexane diisocyanate, 4,4'-dicyclohexylmethane diisocyanate, 1,4-bis(isocyanatomethyl)cyclohexane, and 1,3-bis(isocyanatomethyl)cyclohexane; and aromatic diisocyanates, such as xylylene diisocyanate, 4,4'-diphenyl diisocyanate, 2,4-tolylene diisocyanate, 2,6-tolylene diisocyanate, m-phenylene diisocyanate, p-phenylene diisocyanate, 4,4'-diphenylmethane diisocyanate, 4,4'-diphenyldimethylmethane diisocyanate, 4,4'-dibenzyl diisocyanate, dialkyldiphenylmethane diisocyanate, tetraalkyldiphenylmethane diisocyanate, 1,5-naphthylene diisocyanate, 3,3'-dimethyl-4,4'-biphenylene diisocyanate, polymethylene polyphenylisocyanate, phenylene diisocyanate, and m-tetramethylxylylene diisocyanate. These compounds may be used singly, or in combination of two or more thereof.

Thereamong, 4,4'-diphenylmethane diisocyanate, hexamethylene diisocyanate, 4,4'-dicyclohexylmethane diisocyanate, and isophorone diisocyanate are preferred since these diisocyanates allow the resulting polyurethane to have a good balance of physical properties and are industrially and inexpensively available in large amounts.

<2-2. Chain Extender>

The chain extender used in the polyurethane production is a low-molecular-weight compound which has at least two active hydrogens reacting with isocyanate groups in the production of the below-described isocyanate group-containing prepolymer, and the chain extender is usually, for example, a polyol or a polyamine.

Specific examples thereof include linear diols, such as ethylene glycol, 1,3-propanediol, 1,4-butanediol, 1,5-pentanediol, 1,6-hexanediol, 1,8-octanediol, 1,9-nonanediol, 1,10-decanediol, and 1,12-dodecanediol; branched chain-containing diols, such as 2-methyl-1,3-propanediol, 2,2-dimethyl-1,3-propanediol, 2,2-diethyl-1,3-propanediol, 2-methyl-2-propyl-1,3-propanediol, 2-methyl-1,4-butanediol, 2,4-heptanediol, 1,4-dimethylolhexane, 2-ethyl-1,3-hexanediol, 2,2,4-trimethyl-1,3-pentanediol, 2-methyl-1,8-octanediol, 2-butyl-2-ethyl-1,3-propanediol, and dimer diol; ether group-containing diols, such as diethylene glycol and propylene glycol; diols having an alicyclic structure, such as 1,4-cyclohexanediol, 1,4-cyclohexanedimethanol, and 1,4-dihydroxyethylcyclohexane; aromatic group-containing diols, such as xylylene glycol, 1,4-dihydroxyethylbenzene, and 4,4'-methylenebis(hydroxyethylbenzene); polyols, such as glycerin, trimethylolpropane, and pentaerythritol; hydroxyamines, such as N-methylethanolamine and N-ethylethanolamine; polyamines, such as ethylene diamine, 1,3-diaminopropane, hexamethylene diamine, triethylene tetramine, diethylene triamine, isophorone diamine, 4,4'-diaminodicyclohexylmethane, 2-hydroxyethylpropylene diamine, di-2-hydroxyethylethylene diamine, di-2-hydroxyethylpropylene diamine, 2-hydroxypropylethylene diamine, di-2-hydroxypropylethylene diamine, 4,4'-diphenylmethane diamine, methylene-bis(o-chloroaniline), xylylene diamine, diphenyl diamine, tolylene diamine, hydrazine, piperazine, and N,N'-diaminopiperazine; and water.

These chain extenders may be used singly, or in combination of two or more thereof. Thereamong, 1,4-butanediol, 1,5-pentanediol, 1,6-hexanediol, 1,8-octanediol, 1,9-nonanediol, 1,10-decanediol, 1,4-cyclohexanedimethanol, 1,4-dihydroxyethylcyclohexane, ethylenediamine, 1,3-diaminopropane, isophoronediamine, and 4,4'-diaminodicyclohexylmethane are preferred since these chain extenders allow the resulting polyurethane to have a good balance of physical properties and are industrially and inexpensively available in large amounts.

Further, the chain extender used in the production of the below-described hydroxy group-containing prepolymer is a low-molecular-weight compound having at least two isocyanate groups, and specific examples thereof include those compounds exemplified in <2-1. Polyisocyanate>.

<2-3. Chain Terminator>

In the polyurethane production, a chain terminator having one active hydrogen group may be used as required for the purpose of controlling the molecular weight of the resulting polyurethane.

Examples of the chain terminator include aliphatic monools having one hydroxy group, such as methanol, ethanol, propanol, butanol, and hexanol; and aliphatic monoamines having one amino group, such as diethylamine, dibutylamine, n-butylamine, monoethanolamine, diethanolamine, and morpholine.

These chain terminators may be used singly, or in combination of two or more thereof.

<2-4. Catalyst>

In a polyurethane-forming reaction performed in the polyurethane production, a known urethane polymerization catalyst may be used, and representative examples thereof include amine-based catalysts, such as triethylamine, N-ethylmorpholine, and triethylenediamine; acid-based catalysts, such as acetic acid, phosphoric acid, sulfuric acid, hydrochloric acid, and sulfonic acid; and organic metal salts, for example, tin-based compounds, such as trimethyl tin laurate, dibutyl tin dilaurate, dioctyl tin dilaurate and dioctyl tin dineodecanoate, and titanium-based compounds. These urethane polymerization catalysts may be used singly, or in combination of two or more thereof.

<2-5. Polyol other than Polycarbonate Polyol according to One Aspect of Present Invention>

In the polyurethane-forming reaction performed in the production of the polyurethane according to one aspect of the present invention, the polycarbonate polyol according to one aspect of the present invention may be used in combination with a polyol other than the polycarbonate polyol (hereinafter, may be referred to as "other polyol") as required. It is noted here that this other polyol is not particularly restricted as long as it is usually used in the production of a polyurethane, and examples thereof include polyether polyols, polyester polyols, polycaprolactone polyols, and polycarbonate polyols other than the polycarbonate polyol according to one aspect of the present invention. For example, when a polyether polyol is used in combination, a polyurethane having a further improved flexibility, which is a characteristic feature of the polycarbonate polyol, can be obtained. The weight ratio of the polycarbonate polyol according to one aspect of the present invention with respect to a total weight of the polycarbonate polyol according to one aspect of the present invention and other polyol is preferably 70% or higher, more preferably 90% or higher. When the weight ratio of the polycarbonate polyol according to one aspect of the present invention is small, the balance of the flexibility and the solvent resistance, which is a characteristic feature of the polycarbonate polyol according to one aspect of the present invention, may be lost.

<2-6. Modification of Polycarbonate Diol>

In the present invention, the polycarbonate polyol according to one aspect of the present invention may be modified and then used for the polyurethane production. Examples of a method of modifying the polycarbonate polyol include a method of introducing an ether group to the polycarbonate polyol by an addition of an epoxy compound, such as ethylene oxide, propylene oxide or butylene oxide; and a method of introducing an ester group by allowing the polycarbonate polyol to react with a cyclic lactone such as ε-caprolactone, a dicarboxylic acid compound such as adipic acid, succinic acid, sebacic acid or terephthalic acid, and an ester compound thereof. In ether modification, the viscosity of the polycarbonate polyol is reduced by the modification with ethylene oxide, propylene oxide or the like, and ether modification is preferred because of the ease of handling and the like. Particularly, the modification of the polycarbonate polyol with ethylene oxide or propylene oxide leads to a reduction in the crystallinity of the polycarbonate polyol and an improvement in the flexibility at low temperatures and, in the case of the modification with ethylene oxide, since the water absorption and the moisture permeability of a polyurethane produced using the ethylene oxide-modified polycarbonate polyol are enhanced, the performance of the polyurethane as an artificial leather, a synthetic leather or the like may be improved. However, when the amount of added ethylene oxide or propylene oxide is large, various physical properties of the polyurethane produced using the modified polycarbonate polyol, such as mechanical strength, heat resistance and solvent resistance, are deteriorated; therefore, the amount of ethylene oxide or propylene oxide added to the polycarbonate polyol is suitably 5 to 50% by weight, preferably 5 to 40% by weight, more preferably 5 to 30% by weight. Moreover, in the method of introducing an ester group, the viscosity of the polycarbonate polyol is reduced by the modification with ε-caprolactone, and this method is also preferred because of the ease of handling and the like. The amount of ε-caprolactone added to the polycarbonate polyol is suitably 5 to 50% by weight, preferably 5 to 40% by weight, more preferably 5 to 30% by weight. When the amount of added ε-caprolactone is greater than 50% by weight, the hydrolysis resistance, the chemical resistance and the like of the polyurethane produced using the modified polycarbonate polyol are reduced.

<2-7. Solvent>

In the polyurethane-forming reaction performed in the production of the polyurethane according to one aspect of the present invention, a solvent may be used.

Examples of a preferred solvent include amide-based solvents, such as dimethylformamide, diethylformamide, dimethylacetamide, and N-methylpyrrolidone; sulfoxide-based solvents, such as dimethyl sulfoxide; ketone-based solvents, such as methyl ethyl ketone, cyclohexanone, and methyl isobutyl ketone; ether-based solvents, such as tetrahydrofuran and dioxane; ester-based solvents, such as methyl acetate, ethyl acetate, and butyl acetate; and aromatic hydrocarbon-based solvents, such as toluene and xylene. Any of these solvents may be used singly, or two or more thereof may be used as a mixed solvent.

Thereamong, preferred organic solvents are, for example, dimethylformamide, dimethylacetamide, N-methylpyrrolidone, dimethyl sulfoxide, methyl ethyl ketone, ethyl acetate, and toluene.

Further, a polyurethane in the form of an aqueous dispersion can be produced from a polyurethane composition in which the polycarbonate polyol according to one aspect of the present invention, a polydiisocyanate and the above-described chain extender are blended.

<2-8. Method of Producing Polyurethane>

As a method of producing the polyurethane according to one aspect of the present invention using the above-described reagents, any production method that is used experimentally or industrially in general can be employed.

Examples thereof include a method in which the polycarbonate polyol according to one aspect of the present invention, other polyol used as required, a polyisocyanate and a chain extender are mixed all at once and thereby allowed to react (this method may be hereinafter referred to as "one-step method"); and a method in which the polycarbonate polyol according to one aspect of the present invention, other polyol and a polyisocyanate are allowed to react first so as to prepare a prepolymer having an isocyanate group at both terminals, and this prepolymer is subsequently allowed to react with a chain extender (this method may be hereinafter referred to as "two-step method").

The two-step method involves the step of allowing the polycarbonate polyol according to one aspect of the present invention and other polyol to react with at least one equivalent of a polyisocyanate in advance so as to prepare an intermediate terminated by isocyanate at both terminals, which is a moiety corresponding to the soft segment of a polyurethane. When a prepolymer is prepared once and subsequently allowed to react with a chain extender in this manner, the molecular weight of the soft segment moiety may be easily adjusted, and this is useful in a case where phase separation of the soft segment and the hard segment needs to be ensured.

<2-9. One-Step Method>

The one-step method, which is also called "one-shot method", is a method of performing a reaction by charging the polycarbonate polyol according to one aspect of the present invention, other polyol, a polyisocyanate and a chain extender all at once.

The amount of the polyisocyanate to be used in the one-step method is not particularly restricted; however, when the sum of the total number of hydroxy groups in the polycarbonate polyol according to one aspect of the present invention and other polyol and the number of hydroxy groups and amino groups in the chain extender is assumed to be 1 equivalent, the lower limit of the amount of the polyisocyanate is preferably 0.5 equivalents, more preferably 0.6 equivalents, still more preferably 0.7 equivalents, particularly preferably 0.8 equivalents, while the upper limit is preferably 2.0 equivalents, more preferably 1.5 equivalents, still more preferably 1.2 equivalents, particularly preferably 1.0 equivalent.

It is noted here that the equivalent ratio of the total number of all isocyanate groups, all hydroxy groups and all amino groups that are derived from the above-described raw materials to be used may be hereinafter referred to as "NCO/OH ratio".

When the polyisocyanate is used in an excessively large amount, unreacted isocyanate groups induce side reactions, and this tends to make it difficult to handle the resulting polyurethane and impair the flexibility of the polyurethane due to an excessively high viscosity, whereas when the amount of the polyisocyanate is excessively small, since the molecular weight is not sufficiently increased in the resulting polyurethane, the polyurethane tends to have insufficient strength and solvent resistance.

The amount of the chain extender to be used is also not particularly restricted; however, when the value obtained by subtracting the number of isocyanate groups in the polyisocyanate from the total number of hydroxy groups in the polycarbonate polyol according to one aspect of the present invention and other polyol is assumed to be 1 equivalent, the lower limit of the amount of the chain extender is preferably 0.7 equivalents, more preferably 0.8 equivalents, still more preferably 0.9 equivalents, particularly preferably 0.95 equivalents, while the upper limit is preferably 3.0 equivalents, more preferably 2.0 equivalents, still more preferably 1.5 equivalents, particularly preferably 1.1 equivalents. An excessively large amount of the chain extender tends to make the resulting polyurethane hardly soluble in solvents, thus making the processing of the polyurethane difficult, whereas when the amount of the chain extender is excessively small, since the resulting polyurethane is overly soft, there are cases where sufficient strength, sufficient hardness and sufficient elasticity-recovering and elasticity-retaining performance are not attained, or the heat resistance is deteriorated.

<2-10. Two-Step Method>

The two-step method is also called "prepolymer method", and examples thereof mainly include the following methods:

(a) a method in which a prepolymer having isocyanate groups at molecular chain terminals is prepared in advance by allowing the polycarbonate polyol according to one aspect of the present invention and other polyol to react with an excess amount of a polyisocyanate at a reaction equivalent ratio (polyisocyanate/(polycarbonate polyol according to one aspect of the present invention and other polyol)) of higher than 1 to 10.0, and a chain extender is subsequently added to the prepolymer to produce a polyurethane; and (b) a method in which a prepolymer having hydroxy groups at molecular chain terminals is prepared in advance by allowing a polyisocyanate to react with an excess amount of the polycarbonate polyol according to one aspect of the present invention and other polyol at a reaction equivalent ratio (polyisocyanate/(polycarbonate polyol according to one aspect of the present invention and other polyol)) of 0.1 to less than 1.0 and, as a chain extender, an isocyanate group-terminated polyisocyanate is subsequently allowed to react with the prepolymer so as to produce a polyurethane.

The two-step method can be carried out in the absence or presence of a solvent.

The polyurethane production based on the two-step method can be performed by any of the following methods (1) to (3):

(1) a method in which a prepolymer is synthesized first by allowing a polyisocyanate, the polycarbonate polyol according to one aspect of the present invention and other polyol to directly react with each other without using a solvent, and the prepolymer is used as is for a chain extension reaction;

(2) a method in which a prepolymer is synthesized in the same manner as in the method (1) and subsequently dissolved in a solvent, and the resultant is used for the subsequent chain extension reaction; and (3) a method in which a polyisocyanate, the polycarbonate polyol according to one aspect of the present invention and other polyol are allowed to react with each other using a solvent from the beginning, followed by a chain extension reaction.

In the case of the method (1), it is important to obtain a polyurethane in the form of coexisting with a solvent by, for example, dissolving the chain extender in the solvent or simultaneously dissolving the prepolymer and the chain extender in the solvent at the time of performing the chain extension reaction.

The amount of the polyisocyanate to be used in the two-step method (a) is not particularly restricted; however, when the total number of hydroxy groups in the polycarbonate polyol according to one aspect of the present invention and other polyol is assumed to be 1 equivalent, the amount of the polyisocyanate in terms of the number of isocyanate groups is in a range where the lower limit is preferably 1.0 equivalent or greater, more preferably 1.2 equivalents, still more preferably 1.5 equivalents, while the upper limit is preferably 10.0 equivalents, more preferably 5.0 equivalents, still more preferably 3.0 equivalents.

When the amount of this isocyanate is excessively large, excess isocyanate groups induce side reactions and this tends to make the resulting polyurethane unlikely to achieve desired physical properties (e.g., an excessive increase in the viscosity tends to reduce the flexibility of the polyurethane, and the productivity tends to be deteriorated due to poor ease of handling), whereas when the amount is excessively small, since the molecular weight is not sufficiently increased in the resulting polyurethane, the polyurethane may have a low strength and poor thermal stability.

The amount of the chain extender to be used is also not particularly restricted; however, with respect to 1 equivalent of the isocyanate groups contained in the prepolymer, the lower limit of the amount of the chain extender is preferably 0.1 equivalents, more preferably 0.5 equivalents, still more preferably 0.8 equivalents, while the upper limit is preferably 5.0 equivalents, more preferably 3.0 equivalents, still more preferably 2.0 equivalents.

At the time of performing the above-described chain extension reaction, a monofunctional organic amine or an alcohol may be allowed to coexist for the purpose of adjusting the molecular weight.

In the preparation of a hydroxy group-terminated prepolymer in the two-step method (b), the amount of the polyisocyanate to be used is not particularly restricted; however, when the total number of hydroxy groups in the polycarbonate polyol and other polyol is assumed to be 1 equivalent, the lower limit of the number of isocyanate groups is preferably 0.1 equivalents, more preferably 0.5 equivalents, still more preferably 0.7 equivalents, while the upper limit is preferably 0.99 equivalents, more preferably 0.98 equivalents, still more preferably 0.97 equivalents.

When the amount of this isocyanate is excessively small, the process until the desired molecular weight is attained in the subsequent chain extension reaction takes a long time and the production efficiency thus tends to be reduced, whereas when the amount is excessively large, an excessive increase in the viscosity may reduce the flexibility of the resulting polyurethane, and the productivity may be deteriorated due to poor ease of handling.

The amount of the chain extender to be used is not particularly restricted; however, when the total number of hydroxy groups in the polycarbonate polyol and other polyol used for the prepolymer is assumed to be 1 equivalent, the amount of the chain extender in terms of the total equivalent including the isocyanate groups used for the prepolymer is in a range where the lower limit is preferably 0.7 equivalents, more preferably 0.8 equivalents, still more preferably 0.9 equivalents, while the upper limit is preferably 1.0 equivalent, more preferably 0.99 equivalents, still more preferably 0.98 equivalents.

At the time of performing the above-described chain extension reaction, a monofunctional organic amine or an alcohol may be allowed to coexist for the purpose of adjusting the molecular weight.

The chain extension reaction is usually performed at 0° C. to 250° C.; however, this temperature is not particularly restricted and varies depending on, for example, the amount of the solvent, the reactivity of the raw materials being used, and the reaction equipment. When the temperature is excessively low, the reaction may proceed slowly or the production time may be prolonged due to low solubility of the raw materials or polymerization product, whereas when the temperature is excessively high, a side reaction and decomposition of the resulting polyurethane may occur. The chain extension reaction may be performed while defoaming the resultant under a reduced pressure.

Further, in the chain extension reaction, a catalyst, a stabilizer and the like may also be added as required.

Examples of the catalyst include compounds such as triethylamine, tributylamine, dibutyl tin dilaurate, stannous octoate, acetic acid, phosphoric acid, sulfuric acid, hydrochloric acid and sulfonic acid, and these compounds may be used singly, or in combination of two or more thereof. Examples of the stabilizer include compounds such as 2,6-dibutyl-4-methylphenol, distearyl thiodipropionate, N,N'-di-2-naphthyl-1,4-phenylenediamine and tris(dinonylphenyl)phosphite, and these compounds may be used singly, or in combination of two or more thereof. It is noted here that, when the chain extender is a highly reactive compound such as a short-chain aliphatic amine, the chain extension reaction may be performed without adding a catalyst.

<2-11. Aqueous Polyurethane Emulsion>

An aqueous polyurethane emulsion can be produced using the polycarbonate polyol according to one aspect of the present invention.

In this case, at the time of producing a prepolymer by allowing polyols including the polycarbonate polyol and an excess amount of a polyisocyanate to react with each other, the prepolymer is formed while mixing a compound having at least one hydrophilic functional group and at least two isocyanate-reactive groups, and the thus obtained prepolymer is subjected to the step of forming a neutral salt of the hydrophilic functional group, the emulsification step with an addition of water, and the chain extension reaction step, whereby an aqueous polyurethane emulsion is produced.

In the compound having at least one hydrophilic functional group and at least two isocyanate-reactive groups that is used in this case, the "hydrophilic functional group" is, for example, a carboxyl group or a sulfonic acid group that is neutralizable with an alkaline group. Further, the "isocyanate-reactive groups" are groups that generally react with an isocyanate to form a urethane bond or a urea bond, such as a hydroxyl group, a primary amino group and a secondary amino group, and these groups may coexist in the same molecule.

Specific examples of the compound having at least one hydrophilic functional group and at least two isocyanate-reactive groups include 2,2'-dimethylolpropionic acid, 2,2-methylolbutyric acid, 2,2'-dimethylolvaleric acid, and diaminocarboxylic acids such as lysine, cystine, and 3,5-diaminocarboxylic acid. These compounds may be used singly, or in combination of two or more thereof. In the actual use of these compounds, they may be neutralized with an alkaline compound, for example, an amine such as trimethylamine, triethylamine, tri-n-propylamine, tributylamine or triethanolamine, sodium hydroxide, potassium hydroxide, or ammonia.

In the case of producing an aqueous polyurethane emulsion, with regard to the amount to be used of the compound having at least one hydrophilic functional group and at least two isocyanate-reactive groups, the lower limit thereof is, for the purpose of increasing the dispersion performance in water, preferably 1% by weight, more preferably 5% by weight, still more preferably 10% by weight, with respect to the total weight of the polycarbonate polyol according to one aspect of the present invention and other polyol. Meanwhile, when the compound is added in an excessively large amount, the properties of the polycarbonate polyol according to one aspect of the present invention are sometimes not maintained; therefore, the upper limit of the amount is preferably 50% by weight, more preferably 40% by weight, still more preferably 30% by weight.

In the case of producing an aqueous polyurethane emulsion, the reaction in the prepolymer-forming step may be performed in the presence of a solvent, such as methyl ethyl ketone, acetone or N-methyl-2-pyrrolidone, or in the absence of a solvent. When a solvent is used, it is preferred to remove the solvent by distillation after the production of an aqueous emulsion.

In the production of an aqueous polyurethane emulsion using the polycarbonate polyol according to one aspect of the present invention as a raw material in the absence of a solvent, the upper limit of the number-average molecular weight of the polycarbonate polyol, which is determined from the hydroxyl value, is preferably 5,000, more preferably 4,500, still more preferably 4,000. Meanwhile, the lower limit of the number-average molecular weight is preferably 300, more preferably 500, still more preferably 800. When the number-average molecular weight determined from the hydroxyl value is higher than 5,000 or less than 300, it may be difficult to perform the emulsification.

For the synthesis or storage of the aqueous polyurethane emulsion, the emulsification stability may be maintained by using in combination, for example, an anionic surfactant typified by higher fatty acids, resin acids, acidic fatty alcohols, sulfuric acid esters, higher alkyl sulfonates, alkylaryl sulfonates, sulfonated castor oil, and sulfosuccinic acid esters; a cationic surfactant, such as a primary amine salt, a secondary amine salt, a tertiary amine salt, a quaternary amine salt, or a pyridinium salt; or a nonionic surfactant typified by known reaction products of ethylene oxide with a long-chain fatty alcohol or a phenol.

In the production of an aqueous polyurethane emulsion, an emulsion can also be produced by, as required, mixing an organic solvent solution of the prepolymer with water under high mechanical shear in the presence of an emulsifier, without the neutral salt-forming step.

The aqueous polyurethane emulsion produced in this manner can be used in various applications. Particularly, a chemical raw material having a small environmental load is demanded recently, and the aqueous polyurethane emulsion can be an alternative to conventional products, aiming at no use of an organic solvent.

With regard to the specific use of the aqueous polyurethane emulsion, for example, the aqueous polyurethane emulsion is suitably utilized for coating agents, aqueous paints, adhesives, synthetic leathers, and artificial leathers. Particularly, an aqueous polyurethane emulsion produced using the polycarbonate polyol according to one aspect of the present invention contains a structural unit derived from the oxyalkylene glycol (A1) in the polycarbonate polyol and, therefore, is flexible and can thus be effectively utilized as a coating agent and the like.

<2-12. Additives>

In the polyurethane produced using the polycarbonate polyol, a variety of additives, such as a thermal stabilizer, a light stabilizer, a coloring agent, a bulking agent, a stabilizer, a UV absorber, an antioxidant, an adhesion inhibitor, a flame retardant, an age resistor and an inorganic filler, can be added and mixed within a range that does not impair the properties of the polyurethane.

Examples of a compound that can be used as the thermal stabilizer include phosphorus compounds, such as aliphatic, aromatic or alkyl group-substituted aromatic esters of phosphoric acid or phosphorous acid, hypophosphorous acid derivatives, phenylphosphonic acid, phenylphosphinic acid, diphenylphosphonic acid, polyphosphonates, dialkylpentaerythritol diphosphite, and dialkyl bisphenol-A diphosphite; phenolic derivatives, particularly hindered phenol compounds; sulfur-containing compounds, such as thioether-based, dithioate-based, mercaptobenzimidazole-based, thiocarbanilide-based and thiodipropionic acid ester-based compounds; and tin-based compounds, such as tin maleate and dibutyl tin monoxide.

Specific examples of the hindered phenol compounds include "IRGANOX 1010" (trade name: manufactured by BASF Japan, Ltd.), "IRGANOX 1520" (trade name: manufactured by BASF Japan, Ltd.), and "IRGANOX 245" (trade name: manufactured by BASF Japan, Ltd.). Examples of the phosphorus compounds include "PEP-36", "PEP-24G" and "HP-10" (trade names: all of which are manufactured by ADEKA Corporation), and "IRGAFOS 168" (trade name: manufactured by BASF Japan, Ltd.).

Specific examples of the sulfur-containing compounds include thioether compounds, such as dilauryl thiopropionate (DLTP) and distearyl thiopropionate (DSTP).

Examples of the light stabilizer include benzotriazole-based and benzophenone-based compounds and, specifically, for example, "TINUVIN 622LD" and "TINUVIN 765" (which are manufactured by Ciba Specialty Chemicals Holding Inc.) as well as "SANOL LS-2626" and "SANOL LS-765" (which are manufactured by Sankyo Co., Ltd.) can be used.

Examples of the UV absorber include "TINUVIN 328" and "TINUVIN 234" (which are manufactured by Ciba Specialty Chemicals Holding Inc.).

Examples of the coloring agent include dyes, such as direct dyes, acid dyes, basic dyes, and metal complex salt dyes; inorganic pigments, such as carbon black, titanium oxide, zinc oxide, iron oxide, and mica; and organic pigments, such as coupling azo-based, condensed azo-based, anthraquinone-based, thioindigo-based, dioxazone-based and phthalocyanine-based pigments.

Examples of the inorganic filler include short glass fibers, carbon fibers, alumina, talc, graphite, melamine, and white clay.

Examples of the flame retardant include organic compounds containing phosphorus and halogen, organic compounds containing bromine or chlorine, and additive-type and reactive-type flame retardants, such as ammonium polyphosphate, aluminum hydroxide, and antimony oxide.

Any of the above-described additives may be used singly, or two or more thereof may be used in any combination at any ratio.

As for the amount of these additives to be added in terms of weight ratio with respect to the polyurethane, the lower limit is preferably 0.01% by weight, more preferably 0.05% by weight, still more preferably 0.1% by weight, while the upper limit is preferably 10% by weight, more preferably 5% by weight, still more preferably 1% by weight. When the amount of the additives is excessively small, the effect of the addition cannot be sufficiently obtained, whereas the amount is excessively large, the additives may precipitate in the polyurethane or cause turbidity.

<2-13. Polyurethane Film and Polyurethane Plate>

In the case of producing a film using the polyurethane according to one aspect of the present invention, the lower limit of the film thickness is preferably 10 µm, more preferably 20 µm, still more preferably 30 µm, while the upper limit is preferably 1,000 µm, more preferably 500 µm, still more preferably 100 µm.

When the film is excessively thick, sufficient moisture permeability is unlikely to be attained, whereas an excessively small thickness tends to result in the formation of pinholes, and blocking is likely to occur in such a film, making the handling of the film difficult.

<2-14. Molecular Weight>

The molecular weight of the polyurethane according to one aspect of the present invention is adjusted as appropriate in accordance with the intended used and is not particularly restricted; however, the weight-average molecular weight (Mw) in terms of polystyrene, which is determined by gel permeation chromatography (GPC), is preferably 50,000 to 500,000, more preferably 100,000 to 300,000. When the Mw is less than the lower limit, sufficient strength and hardness are sometimes not attained, whereas when the Mw is higher than the upper limit, the ease of handling such as processability tends to be deteriorated. Particularly, by using the polycarbonate polyol according to one aspect of the present invention, a polyurethane having an Mw of 100,000 or higher can be easily produced because of the excellent reactivity of the polycarbonate polyol, and a sufficient mechanical strength can be attained.

<2-15. Solvent Resistance>
<2-15-1. Oleic Acid Resistance>

In the evaluation of the polyurethane according to one aspect of the present invention by, for example, the method described below in the section of Examples, the rate of change (%) in the weight of a polyurethane test piece after immersion in oleic acid with respect to the weight of the polyurethane test piece before immersion in oleic acid is preferably 20% or lower, more preferably 10% or lower, still more preferably 5% or lower, particularly preferably 4% or lower, most preferably 3% or lower.

When this weight change rate is higher than the upper limit, sufficient oleic acid resistance may not be attained.

<2-15-2. Ethanol Resistance>

In the evaluation of the polyurethane according to one aspect of the present invention by, for example, the method described below in the section of Examples, the rate of change (%) in the weight of a polyurethane test piece after immersion in ethanol with respect to the weight of the polyurethane test piece before immersion in ethanol is preferably 20% or lower, more preferably 18% or lower, still more preferably 15% or lower, particularly preferably 10% or lower, most preferably 8% or lower.

When this weight change rate is higher than the upper limit, sufficient ethanol resistance may not be attained.

<2-15-3. Ethyl Acetate Resistance>

In the evaluation of the polyurethane according to one aspect of the present invention by, for example, the method described below in the section of Examples, the rate of change (%) in the weight of a polyurethane test piece after immersion in ethyl acetate with respect to the weight of the polyurethane test piece before immersion in ethyl acetate is preferably 50% or lower, more preferably 40% or lower, still more preferably 35% or lower. When this weight change rate is higher than the upper limit, the desired ethyl acetate resistance may not be attained.

<2-16. Tensile Elongation at Break>

The tensile elongation at break and the breaking strength of the polyurethane according to one aspect of the present invention, which are measured for a strip-form sample of 10 mm in width, 100 mm in length and about 50 to 100 μm in thickness under the conditions of a chuck distance of 50 mm and a tensile rate of 500 mm/min at a temperature of 23° C. and a relative humidity of 50%, are preferably in the following respective ranges.

That is, the lower limit of the elongation at break is preferably 150%, more preferably 200%, still more preferably 300%, while the upper limit is preferably 3,000%, more preferably 2,000%, still more preferably 1,500%. When the elongation at break is less than the lower limit, the ease of handling such as processability tends to be deteriorated, whereas when the elongation at break is higher than the upper limit, sufficient solvent resistance may not be attained.

Further, the lower limit of the breaking strength is preferably 1.0 MPa, more preferably 2.0 MPa, still more preferably 3.0 MPa, while the upper limit is preferably 100 MPa, more preferably 8.0 MPa, still more preferably 6.0 MPa. When the breaking strength is less than the lower limit, the ease of handling such as processability tends to be deterio-rated, whereas when the breaking strength is higher than the upper limit, the flexibility may be deteriorated.

<2-17. 100% Modulus and 300% Modulus>

In the polyurethane according to one aspect of the present invention, when the polyurethane is obtained by a one-step method where the polycarbonate polyol according to one aspect of the present invention is allowed to react with 4,4'-diphenylmethane diisocyanate and 1,4-butanediol such that the total amount of 4,4'-diphenylmethane diisocyanate and 1,4-butanediol is 17 to 20% by weight with respect to the whole amount of the polyurethane, the 100% modulus and the 300% modulus, which are measured for a strip-form sample of 10 mm in width, 100 mm in length and about 50 to 100 μm in thickness under the conditions of a chuck distance of 50 mm and a tensile rate of 500 mm/min at a temperature of 23° C. and a relative humidity of 50%, are preferably in the following respective ranges.

That is, the lower limit of the 100% modulus is preferably 0.7 MPa, more preferably 0.9 MPa, still more preferably 1.0 MPa, while the upper limit is preferably 20 MPa, more preferably 10 MPa, still more preferably 5.0 MPa. When the 100% modulus is less than the lower limit, the solvent resistance may be insufficient, whereas when the 100% modulus is higher than the upper limit, the flexibility may be insufficient, and the ease of handling such as processability tends to be deteriorated.

Further, the lower limit of the 300% modulus is preferably 1.4 MPa, more preferably 2.0 MPa, still more preferably 2.5 MPa, while the upper limit is preferably 15 MPa, more preferably 9.0 MPa, still more preferably 6.0 MPa. When the 300% modulus is less than the lower limit, the solvent resistance may be insufficient, whereas when the 300% modulus is higher than the upper limit, the flexibility may be insufficient, and the ease of handling such as processability tends to be deteriorated.

<2-18. Glass Transition Temperature>

As for the glass transition temperature of the polyurethane according to one aspect of the present invention, the lower limit is usually −70° C., preferably −60° C., more preferably −50° C., still more preferably −40° C., particularly preferably −30° C., while the upper limit is usually 0° C., preferably −5° C., more preferably −10° C., still more preferably −15° C., particularly preferably −20° C. When the glass transition temperature of the polyurethane is not lower than the lower limit, good solvent resistance is attained and, by controlling the glass transition temperature to be not higher than the upper limit, hardening of the polyurethane at low temperatures is inhibited, so that the texture tends to be improved.

<2-19. Use>

The polyurethane has excellent solvent resistance and good flexibility and mechanical strength and, therefore, can be widely used for, for example, foams, elastomers, elastic fibers, coating materials, fibers, pressure-sensitive adhesives, adhesives, floor materials, sealants, medical materials, artificial leathers, synthetic leathers, coating agents, aqueous polyurethane paints, and active energy ray-curable polymer compositions.

Particularly, when the polyurethane is used in applications such as artificial leathers, synthetic leathers, aqueous polyurethane, adhesives, elastic fibers, medical materials, floor materials, paints and coating agents, since the polyurethane has a good balance of solvent resistance, flexibility and mechanical strength, the polyurethane can impart favorable characteristics, such as high durability, sufficient flexibility and excellent strength against physical impact and the like, to those parts which come into contact with human skin or where a cosmetic preparation or a rubbing alcohol is used. Moreover, the polyurethane can also be suitably used in automobile applications such as automobile members where heat resistance is required, as well as outdoor applications where weather resistance is required.

The polyurethane can be used for a cast polyurethane elastomer. Specific applications thereof include rolls, such as press-rolling rolls, papermaking rolls, office equipments, pre-tension rolls, printing rolls, and coater rolls; solid tires and casters of fork lifts, motor vehicle new trams, wheeled carriers, trucks and the like; and industrial products, such as conveyor belt idlers, guide rolls, pulleys, steel pipe linings, ore rubber screens, gears, connection rings, liners, pump impellers, cyclone cones, and cyclone liners. In addition, the polyurethane can also be used in belts of OA devices, paper feed rolls, copier cleaning blades, snowplows, toothed belts, surf rollers, and the like.

The polyurethane is also applied as a thermoplastic elastomer. The polyurethane can be used for, for example, tubes and hoses in pneumatic instruments employed in the food and medical fields, coating apparatuses, analytical instruments, physicochemical instruments, metering pumps, water treatment apparatuses and industrial robots, as well as spiral tubes and fire hoses. The polyurethane can also be used as a belt, such as a round belt, a V-belt or a flat belt, in various transmission mechanisms, spinning machines, packaging machines, printing machines, and the like. Further, the polyurethane can be used in footwear heel tops, shoe soles, machine components (e.g., couplings, packings, ball joints, bushes, gears, and roll), sporting goods, leisure goods, watchbands, and the like. Moreover, the polyurethane can be used in automobile components, such as oil stoppers, gearboxes, spacers, chassis parts, interior trims, and tire chain substitutes. Furthermore, the polyurethane can be used in films, such as keyboard films and automotive films, curl codes, cable sheaths, bellows, conveyor belts, flexible containers, binders, synthetic leathers, dipping products, adhesives, and the like.

The polyurethane is also applicable to the use as a solvent-based two-component paint and may be applied to wood products, such as musical instruments, family altars, furniture, decorative plywoods, and sporting equipments. In addition, the polyurethane can be used as a tar-epoxy urethane for automobile repair.

The polyurethane can be used as a component of, for example, moisture-curable one-component paints, blocked isocyanate-based solvent paints, alkyd resin paints, urethane-modified synthetic resin paints, UV-curable paints and aqueous urethane paints, and can be applied to, for example, coating materials for plastic bumpers; strippable paints; coating agents for magnetic tapes; over-print varnishes of floor tiles, floor materials, papers, wood-grain printed films and the like; varnishes for wood materials; high-processing coil coatings; optical fiber protective coatings; solder resists; topcoats for metal printing; basecoats for vapor deposition; and whitecoats for food cans.

Further, the polyurethane can be applied as a pressure-sensitive adhesive or an adhesive for food packagings, shoes, footwear, magnetic tape binders, decorative papers, wood materials, structural members and the like, and can also be used as a component of low-temperature adhesives and hot-melts.

The polyurethane can be used as a binder in, for example, magnetic recording media, inks, castings, fired bricks, graft materials, microcapsules, granular fertilizers, granular agricultural chemicals, polymer cement mortars, resin mortars, rubber chip binders, recycled foam, and glass fiber sizings.

The polyurethane can also be used as a component of a fiber-processing agent for shrink proofing, crease proofing, water repellent finishing, and the like.

In the case of using the polyurethane as an elastic fiber, fibrillization thereof can be performed by any method with no particular restriction as long as the method is capable of spinning the polyurethane. For example, a melt-spinning method in which the polyurethane is made into a pellet once and this pellet is subsequently melted and spun directly through a spinneret may be employed. When the elastic fiber is obtained from the polyurethane by melt-spinning, the spinning temperature is preferably 250° C. or lower, more preferably 200° C. to 235° C.

The polyurethane elastic fiber can be used directly as a bare fiber, or may be coated with other fiber and used as a coated fiber. Examples of such other fiber include conventionally known fibers, such as polyamide fibers, wool, cotton and polyester fibers, among which a polyester fiber is preferably used in the present invention. Further, the elastic fiber using the polyurethane may contain a dyeing-type disperse dye as well.

The polyurethane can be used as a sealant or caulking for, for example, concrete walls, control joints, sash peripheries, wall-type PC (precast concrete) joints, ALC (autoclaved light-weight concrete) joints, board joints, composite glass sealants, heat-insulating sash sealants, and automotive sealants.

The polyurethane can be used as a medical material and may be used as a blood compatible material for tubes, catheters, artificial hearts, artificial blood vessels, artificial valves and the like, or as a disposable material for catheters, tubes, bags, surgical gloves, artificial kidney potting materials and the like. The polyurethane, through modification of its terminals, can also be used as a raw material for, for example, UV-curable paints, electron beam-curable paints, photosensitive resin compositions for flexographic printing plates, and photocurable coating compositions for optical fibers.

<2-20. Urethane (Meth)acrylate-based Oligomer>

A urethane (meth)acrylate-based oligomer can be produced by an addition reaction of a polyisocyanate and a hydroxyalkyl (meth)acrylate using the polycarbonate polyol according to one aspect of the present invention. When a polyol as other raw material compound, a chain extender and the like are used in combination, a urethane (meth)acrylate-based oligomer can be produced by further adding the other raw material compounds to the polyisocyanate through reaction.

It is noted here that, in the present invention, the term "(meth)acryl" as in "(meth)acrylate" and "(meth)acrylic acid" means acryl and/or methacryl.

In this process, the ratio of each raw material compound to be added is substantially equal to or the same as that in the composition of the desired urethane (meth)acrylate-based oligomer.

The amount of all isocyanate groups in the resulting urethane (meth)acrylate-based oligomer and the amount of all functional groups reacting with the isocyanate groups, such as hydroxy groups and amino groups, are normally equimolar in theory.

In the production of the urethane (meth)acrylate-based oligomer, the amount of the hydroxyalkyl (meth)acrylate to be used is usually not less than 10% by mole, preferably not less than 15% by mole, still more preferably not less than 25% by mole, but usually 70% by mole or less, preferably 50% by mole or less, with respect to the total amount of the hydroxyalkyl (meth)acrylate, the polycarbonatepolyol, the polyol used as other raw material compound as required and a compound containing a functional group reacting with isocyanate, such as a chain extender. The molecular weight of the resulting urethane (meth)acrylate-based oligomer can be controlled in accordance with this ratio. When the ratio of the hydroxyalkyl (meth)acrylate is high, the molecular weight of the urethane (meth)acrylate-based oligomer tends to be small, whereas when the ratio is low, the molecular weight tends to be large.

The amount of the polycarbonate polyol according to one aspect of the present invention to be used is preferably not less than 25% by mole, more preferably not less than 50% by mole, still more preferably not less than 70% by mole, with respect to the total amount of the polycarbonate polyol according to one aspect of the present invention and other polyol. When the polycarbonate polyol according to one aspect of the present invention is used in an amount of not less than the above-described lower limit value, the resulting cured product tends to have favorable elongation, hardness, weather resistance and contamination resistance, which is preferred.

Further, the amount of the polycarbonate polyol according to one aspect of the present invention to be used is preferably not less than 10% by weight, more preferably not less than 30% by weight, still more preferably not less than 50% by weight, particularly preferably not less than 70% by weight, with respect to the total amount of the polycarbonate polyol according to one aspect of the present invention and other polyol. When the polycarbonate polyol according to one aspect of the present invention is used in an amount of not less than the above-described lower limit value, not only the viscosity of the resulting composition is reduced and the workability is thus improved, but also the mechanical strength, hardness and abrasion resistance of the resulting cured product tends to be improved as well, which are preferred.

Moreover, when a chain extender is used, the total amount of the polycarbonate polyol according to one aspect of the present invention and other polyol to be used is preferably not less than 70% by mole, more preferably not less than 80% by mole, still more preferably not less than 90% by mole, particularly preferably not less than 95% by mole, with respect to the total amount of the polycarbonate polyol according to one aspect of the present invention and other polyol in combination with the chain extender. When the polycarbonate polyol according to one aspect of the present invention and other polyol are used in an amount of not less than the above-described lower limit value, the liquid stability tends to be improved, which is preferred.

In the production of the urethane (meth)acrylate-based oligomer, a solvent can be used for the purpose of adjusting the viscosity. A solvent may be used singly, or two or more solvents may be used in combination. As the solvent, any known solvent can be used. Examples of a preferred solvent include toluene, xylene, ethyl acetate, butyl acetate, cyclohexanone, methyl ethyl ketone, and methyl isobutyl ketone. The solvent can be usually used in an amount of less than 300 parts by weight with respect to 100 parts by weight of solid components in the reaction system.

In the production of the urethane (meth)acrylate-based oligomer, the total content of the urethane (meth)acrylate-based oligomer to be produced and the raw material compounds thereof is preferably not less than 20% by weight, more preferably not less than 40% by weight, with respect to the total amount of components in the reaction system. The upper limit of this total content is 100% by weight. When the total content of the urethane (meth)acrylate-based oligomer and the raw material compounds thereof is 20% by weight or greater, the reaction rate is increased and the production efficiency thus tends to be improved, which is preferred.

In the production of the urethane (meth)acrylate-based oligomer, an addition reaction catalyst can be used. Examples of the addition reaction catalyst include dibutyl tin laurate, dibutyl tin dioctoate, dioctyl tin dilaurate, and dioctyl tin dioctoate. These addition reaction catalysts may be used singly, or in combination of two or more thereof. Thereamong, the addition reaction catalyst is preferably dioctyl tin dilaurate from the standpoints of the environmental adaptability, the catalytic activity, and the storage stability.

As for the amount of the addition reaction catalyst to be used, the upper limit thereof is usually 1,000 ppm by weight, preferably 500 ppm by weight, while the lower limit is usually 10 ppm by weight, preferably 30 ppm by weight, with respect to the total content of the urethane (meth)acrylate-based oligomer to be produced and the raw material compounds thereof.

Further, in the production of the urethane (meth)acrylate-based oligomer, when the reaction system contains a (meth)acryloyl group, a polymerization inhibitor can be used in combination. Examples of the polymerization inhibitor include phenols, such as hydroquinone, methylhydroquinone, hydroquinone monoethyl ether, and dibutylhydroxytoluene; amines, such as phenothiazine and diphenylamine; copper salts, such as copper dibutyldithiocarbamate; manganese salts, such as manganese acetate; nitro compounds; and nitroso compounds. These polymerization inhibitors may be used singly, or in combination of two or more thereof. Thereamong, the polymerization inhibitor is preferably a phenol.

As for the amount of the polymerization inhibitor to be used, the upper limit thereof is usually 3,000 ppm, preferably 1,000 ppm by weight, particularly preferably 500 ppm by weight, while the lower limit is usually 50 ppm by weight, preferably 100 ppm by weight, with respect to the total content of the urethane (meth)acrylate-based oligomer to be produced and the raw material compounds thereof.

In the production of the urethane (meth)acrylate-based oligomer, the reaction temperature is usually 20° C. or higher, preferably 40° C. or higher, more preferably 60° C. or higher. When the reaction temperature is 20° C. or higher, the reaction rate is increased and the production efficiency thus tends to be improved, which is preferred. Meanwhile, the reaction temperature is usually 120° C. or lower, preferably 100° C. or lower. When the reaction temperature is 120° C. or lower, a side reaction such as allophanation reaction is unlikely to occur, which is preferred. Further, in cases where the reaction system contains a solvent, the reaction temperature is preferably not higher than the boiling point of the solvent and, in cases where a (meth)acrylate is contained therein, the reaction temperature is preferably 70° C. or lower from the standpoint of inhibiting the reaction of (meth)acryloyl group. The reaction time is usually about 5 to 20 hours.

The number-average molecular weight of the urethane (meth)acrylate-based oligomer obtained in this manner is preferably 500 or higher, particularly preferably 1,000 or higher, but preferably 10,000 or less, particularly preferably 5,000 or less, especially preferably 3,000 or less. When the number-average molecular weight of the urethane (meth)acrylate-based oligomer is not less than the above-described lower limit, a cured film obtained therefrom tends to have good three-dimensional processing suitability and an excellent balance of the three-dimensional processing suitability and the contamination resistance, which is preferred. Meanwhile, when the number-average molecular weight of the urethane (meth)acrylate-based oligomer is not higher than the above-described upper limit, a cured film obtained from the composition thereof tends to have good contamination resistance and an excellent balance of the three-dimensional processing suitability and the contamination resistance, which is preferred. The is presumed to be because the three-dimensional processing suitability and the contamination resistance are dependent on the distance between crosslinking points in a network structure and, when this distance is long, the structure is flexible and elastic and thus provides excellent three-dimensional processing suitability, whereas when the distance is short, the network structure is rigid and thus provides excellent contamination resistance.

<2-21. Polyester-Based Elastomer>

The polycarbonate polyol according to one aspect of the present invention can be used as a polyester-based elastomer. The polyester-based elastomer is a copolymer that is constituted by a hard segment mainly composed of an aromatic polyester and a soft segment mainly composed of an aliphatic polyether, an aliphatic polyester or an aliphatic polycarbonate. When the polycarbonate polyol is used as a constituent of the soft segment, superior physical properties are attained in terms of heat resistance, water resistance and the like as compared to a case where an aliphatic polyether or an aliphatic polyester is used. Even when compared to a known polycarbonate polyol, the polycarbonate polyol exhibits superior fluidity when melted, i.e., a melt flow rate suitable for blow molding and extrusion molding, and yields a polycarbonate ester elastomer having an excellent balance of the mechanical strength and other physical properties, and this polycarbonate ester elastomer can be suitably used in various molding materials including fibers, films and sheets, for example, molding materials for elastic fibers, boots, gears, tubes, and packings.

Specifically, the polycarbonate ester elastomer can be effectively used in applications where heat resistance and durability are required, such as joint boots and wire coating materials of automobiles, home electronic parts and the like.

<2-22. Active Energy Ray-Curable Polymer Composition>

An active energy ray-curable polymer composition containing the above-described urethane (meth)acrylate-based oligomer (hereinafter, may be simply referred to as "active energy ray-curable polymer composition") will now be described.

The active energy ray-curable polymer composition preferably has a calculated molecular weight between network crosslinking points of 500 to 10,000.

In the present specification, the "calculated molecular weight between network crosslinking points" of a composition indicates an average value of the molecular weight between active energy ray-reactive groups forming a network structure in the entire composition (such groups may be hereinafter referred to as "crosslinking points"). The calculated molecular weight between network crosslinking points correlates with the network area in the formation of a network structure, and the crosslinking density decreases as the calculated molecular weight between network crosslinking points increases. In the reaction based on curing with an active energy ray, a linear polymer is formed by a reaction of a compound having only one active energy ray-reactive group (hereinafter, may be referred to as "monofunctional compound"), while a network structure is formed by a reaction of a compound having two or more active energy ray-reactive groups (hereinafter, may be referred to as "polyfunctional compound").

Therefore, the active energy ray-reactive groups contained in a polyfunctional compound constitute crosslinking points, and the calculated molecular weight between network crosslinking points is determined focusing on the polyfunctional compound having such crosslinking points, while handling a monofunctional compound as a component having an effect of increasing the molecular weight between the crosslinking points of the polyfunctional compound. In addition, the determination of the calculated molecular weight between network crosslinking points is performed with an assumption that the active energy ray-reactive groups all have the same reactivity and irradiation with an active energy ray causes all of the active energy ray-reactive groups to undergo a reaction.

In a composition of a single-polyfunctional-compound system where only one kind of polyfunctional compound undergoes a reaction, the calculated molecular weight between network crosslinking points is twice the average molecular weight per active energy ray-reactive group of the polyfunctional compound. For example, the calculated molecular weight between network crosslinking points is $(1,000/2) \times 2 = 1,000$ for the case of a bifunctional compound having a molecular weight of 1,000, or $(300/3) \times 2 = 200$ for the case of a trifunctional compound having a molecular weight of 300.

In a composition of a polyfunctional-compound-mixture system where plural kinds of polyfunctional compounds undergo a reaction, the calculated molecular weight between network crosslinking points of the composition is an average value of the calculated molecular weights between network crosslinking points that are determined for the respective single-polyfunctional-compound systems with respect to the number of all active energy ray-reactive groups contained in the composition. For example, in a composition composed of a mixture containing 4 mol of a bifunctional compound having a molecular weight of 1,000 and 4 mol of a trifunctional compound having a molecular weight of 300, the number of all active energy ray-reactive groups in the composition is $2 \times 4 + 3 \times 4 = 20$, and the calculated molecular weight between network crosslinking points of the composition is thus $\{(1,000/2) \times 8 + (300/3) \times 12\} \times 2/20 = 520$.

When the composition contains a monofunctional compound, assuming for calculation purposes that the reaction takes place such that an equimolar of a molecular chain formed by linking of the monofunctional compound is positioned in the center of each active energy ray-reactive group (i.e., crosslinking point) of the polyfunctional compounds, the length of the molecular chain increased by the monofunctional compound per crosslinking point, which is attributed to the monofunctional compound, is a half of a value obtained by dividing the total molecular weight of the monofunctional compound by the number of all active energy ray-reactive groups of the polyfunctional compounds in the composition. In this case, since the calculated molecular weight between network crosslinking points is considered to be twice the average molecular weight per crosslinking point, the length increased by the monofunctional compound in terms of the calculated molecular weight between network crosslinking points determined for the polyfunctional compounds is a value obtained by dividing the total molecular weight of the monofunctional compound by the number of all active energy ray-reactive groups of the polyfunctional compounds in the composition.

For example, in a composition composed of a mixture containing 40 mol of a monofunctional compound having a molecular weight 100 and 4 mol of a bifunctional compound having a molecular weight 1,000, since the number of active energy ray-reactive groups of the polyfunctional compound is 2×4=8, the length increased by the monofunctional compound in terms of the calculated molecular weight between network crosslinking points is 100×40/8=500. In other words, the calculated molecular weight between network crosslinking points of the composition is 1,000+500=1,500.

Based on the above, with regard to a mixture containing $M_A$ mol of a monofunctional compound having a molecular weight of $W_A$, $M_B$ mol of an $f_B$-functional compound having a molecular weight of $W_B$ and $M_C$ mol of an $f_C$-functional compound having a molecular weight of $W_C$, the calculated molecular weight between network crosslinking points of the composition can be represented by the following formula:

$$\frac{\left(\frac{W_A M_A}{f_B M_B + f_C M_C} + \frac{2 W_B}{f_B}\right) \times f_B M_B + \left(\frac{W_A M_A}{f_B M_B + f_C M_C} + \frac{2 W_C}{f_C}\right) \times f_C M_C}{f_B M_B + f_C M_C} = \frac{W_A M_A + 2 W_B M_B + 2 W_C M_C}{f_B M_B + f_C M_C}$$

The calculated molecular weight between network crosslinking points of the active energy ray-curable polymer composition, which is determined in the above-described manner, is preferably 500 or higher, more preferably 800 or higher, still more preferably 1,000 or higher, but preferably 10,000 or less, more preferably 8,000 or less, still more preferably 6,000 or less, yet still more preferably 4,000 or less, particularly preferably 3,000 or less.

When the calculated molecular weight between network crosslinking points is 10,000 or less, a cured film obtained from the composition tends to have good contamination resistance and an excellent balance of the three-dimensional processing suitability and the contamination resistance, which is preferred. Meanwhile, when the calculated molecular weight between network crosslinking points is 500 or higher, the resulting cured film tends to have good three-dimensional processing suitability and an excellent balance of the three-dimensional processing suitability and the contamination resistance, which is preferred. The is presumed to be because the three-dimensional processing suitability and the contamination resistance are dependent on the distance between crosslinking points in a network structure and, when this distance is long, the structure is flexible and elastic and thus provides excellent three-dimensional processing suitability, whereas when the distance is short, the network structure is rigid and thus provides excellent contamination resistance.

The active energy ray-curable polymer composition may further contain a component(s) other than the urethane (meth)acrylate-based oligomer. Examples of such other components include an active energy ray-reactive monomer, an active energy ray-curable oligomer, a polymerization initiator, a photosensitizer, an additive, and a solvent.

In the active energy ray-curable polymer composition, the content of the urethane (meth)acrylate-based oligomer is preferably not less than 40% by weight, more preferably not less than 60% by weight, with respect to the total amount of active energy ray-reactive components including the urethane (meth)acrylate-based oligomer. The upper limit value of the content is 100% by weight. When the content of the urethane (meth)acrylate-based oligomer is 40% by weight or more, the composition tends to have favorable curability and exhibit an improved three-dimensional processing suitability when made into a cured product, without an excessive increase in the mechanical strength.

Further, in the active energy ray-curable polymer composition, the higher the content of the urethane (meth)acrylate-based oligomer, the more preferred it is in terms of elongation and film-forming properties; however, a lower content is more preferred in terms of reducing the viscosity. From these standpoints, the content of the urethane (meth)acrylate-basedoligomer is preferably not less than 50% by weight, more preferably not less than 70% by weight, with respect to the total amount of all components including other components in addition to the above-described active energy ray-reactive components. The upper limit value of the content of the urethane (meth)acrylate-based oligomer is 100% by weight, and the content is preferably not higher than this value.

Moreover, in the active energy ray-curable polymer composition, from the standpoints of, for example, achieving excellent curing rate and surface curability of the composition and allowing the composition to leave no tack, the total content of the active energy ray-reactive components including the urethane (meth)acrylate-based oligomer is preferably not less than 60% by weight, more preferably not less than 80% by weight, still more preferably not less than 90% by weight, particularly preferably not less than 95% by weight, with respect to the total amount of the composition. The upper limit of the content is 100% by weight.

As the above-described active energy ray-reactive monomer, any known active energy ray-reactive monomer can be used. Such an active energy ray-reactive monomer is used for the purpose of, for example, adjusting the hydrophilicity/hydrophobicity of the urethane (meth)acrylate-based oligomer and the physical properties, such as hardness and elongation, of a cured product obtained from the resulting composition. Such an active energy ray-reactive monomer may be used singly, or two or more thereof may be used in combination.

Examples of the active energy ray-reactive monomer include vinyl ethers, (meth)acrylamides, and (meth)acrylates, specifically aromatic vinyl-based monomers, such as styrene, α-methylstyrene, α-chlorostyrene, vinyltoluene, and divinylbenzene; vinyl ester monomers, such as vinyl acetate, vinyl butyrate, N-vinylformamide, N-vinylacetamide, N-vinyl-2-pyrrolidone, N-vinylcaprolactam, and divinyl adipate; vinyl ethers, such as ethylvinyl ether and phenylvinyl ether; allyl compounds such as diallyl phthalate, trimethylolpropane diallyl ether, and allyl glycidyl ether; (meth)acrylamides, such as (meth)acrylamide, N,N-dimethylacrylamide, N,N-dimethylmethacrylamide, N-methylol (meth)acrylamide, N-methoxymethyl (meth)acrylamide, N-butoxymethyl (meth)acrylamide, N-t-butyl (meth)acrylamide, (meth)acryloyl morpholine, and methylenebis-(meth)acrylamide; monofunctional (meth)acrylates, such as (meth)acrylic acid, methyl (meth)acrylate, ethyl (meth)acrylate, propyl (meth)acrylate, n-butyl (meth)acrylate, i-butyl (meth)acrylate, t-butyl (meth)acrylate, hexyl (meth)acrylate, 2-ethylhexyl (meth)acrylate, lauryl (meth)acrylate, stearyl (meth)acrylate, tetrahydrofurfuryl (meth)acrylate, morpholyl (meth)acrylate, 2-hydroxyethyl (meth)acrylate, 2-hydroxypropyl (meth)acrylate, 4-hydroxybutyl (meth)acrylate, glycidyl (meth)acrylate, dimethylaminoethyl (meth)acrylate, diethylaminoethyl (meth)acrylate, benzyl (meth)acrylate, cyclohexyl (meth)acrylate, phenoxyethyl (meth)acrylate, tricyclodecane (meth)acrylate, dicyclopentenyl (meth)

acrylate, dicyclopentenyloxyethyl (meth)acylate, dicyclopentanyl (meth)acrylate, allyl (meth)acrylate, 2-ethoxyethyl (meth)acrylate, isobornyl (meth)acrylate, and phenyl (meth)acrylate; and polyfunctional (meth)acrylates, such as ethylene glycol di(meth)acrylate, diethylene glycol di(meth)acrylate, triethylene glycol di(meth)acrylate, tetraethylene glycol di(meth)acrylate, polyethylene glycol (n=5 to 14) di(meth)acrylate, propylene glycol di(meth)acylate, dipropylene glycol di(meth)acrylate, tripropylene glycol di(meth)acrylate, tetrapropylene glycol di(meth)acrylate, polypropylene glycol (n=5 to 14) di(meth)acrylate, 1,3-butylene glycol di(meth)acrylate, 1,4-butanediol di(meth)acrylate, polybutylene glycol (n=3 to 16) di(meth)acrylate, poly(1-methylbutylene glycol) (n=5 to 20) di(meth)acrylate, 1,6-hexanediol di(meth)acrylate, 1,9-nonanediol di (meth)acrylate, neopentyl glycol di(meth)acrylate, hydroxypivalic acid neopentyl glycol di(meth)acrylate, dicyclopentanediol di(meth)acrylate, tricyclodecane di(meth)acrylate, trimethylolpropane tri(meth)acrylate, pentaerythritol tri(meth)acrylate, pentaerythritol tetra(meth)acrylate, ditrimethylolpropane tetra(meth)acrylate, dipentaerythritol tetra(meth)acrylate, dipentaerythritol penta(meth)acrylate, dipentaerythritol hexa(meth)acrylate, trimethylolpropane trioxyethyl (meth)acrylate, trimethylolpropane trioxypropyl (meth)acrylate, trimethylolpropane polyoxyethyl (meth)acrylate, trimethylolpropane polyoxypropyl (meth)acrylate, tris(2-hydroxyethyl)isocyanurate tri(meth)acrylate, tris(2-hydroxyethyl)isocyanurate di(meth)acrylate, ethylene oxide-added bisphenol A di(meth)acrylate, ethylene oxide-added bisphenol F di(meth)acrylate, propylene oxide-added bisphenol A di(meth)acrylate, propylene oxide-added bisphenol F di(meth)acrylate, tricyclodecanedimethanol di(meth)acrylate, bisphenol A epoxy di(meth)acrylate, and bisphenol F epoxy di(meth)acrylate.

Thereamong, particularly in those applications where coatability is required, monofunctional (meth)acrylates having a ring structure in the molecule, such as (meth)acryloylmorpholine, tetrahydrofurfuryl (meth)acrylate, benzyl (meth)acrylate, cyclohexyl (meth)acrylate, trimethylcyclohexyl (meth)acrylate, phenoxyethyl (meth)acrylate, tricyclodecane (meth)acrylate, dicyclopentenyl (meth)acrylate, isobornyl (meth)acrylate and (meth)acrylamide, are preferred and, in those applications where mechanical strength is required in the resulting cured product, polyfunctional (meth)acrylates, such as 1,4-butanediol di(meth)acrylate, 1,6-hexanediol di(meth)acrylate, 1,9-nonanediol di(meth)acrylate, neopentyl glycol di(meth)acrylate, tricyclodecane di(meth)acrylate, trimethylolpropane tri(meth)acrylate, pentaerythritol tri(meth)acrylate, pentaerythritol tetra(meth)acrylate, dipentaerythritol tetra(meth)acrylate, dipentaerythritol penta(meth)acrylate and dipentaerythritol hexa(meth)acrylate, are preferred.

In the active energy ray-curable polymer composition, from the standpoint of adjusting the viscosity of the composition as well as the physical properties of the resulting cured product such as hardness and elongation, the content of the active energy ray-reactive monomer is preferably 50% by weight or less, more preferably 30% by weight or less, still more preferably 20% by weight or less, particularly preferably 10% by weight or less, with respect to the total amount of the composition.

As the above-described energy ray-curable oligomer, such an oligomer may be used singly, or two or more thereof may be used in combination. Examples of the energy ray-curable oligomer include epoxy (meth)acrylate-based oligomers and acryl (meth)acrylate-based oligomers.

In the active energy ray-curable polymer composition, from the standpoint of, for example, enabling to adjust the physical properties of the resulting cured product such as hardness and elongation, the content of the active energy ray-reactive oligomer is preferably 50% by weight or less, more preferably 30% by weight or less, still more preferably 20% by weight or less, particularly preferably 10% by weight or less, with respect to the total amount of the composition.

The above-described polymerization initiator is mainly used for the purpose of, for example, improving the efficiency of initiating a polymerization reaction that proceeds under irradiation with an active energy ray, such as an ultraviolet ray or an electron beam. As the polymerization initiator, a radical photopolymerization initiator that is a compound having a property of generating a radical with light is generally used, and any known radical photopolymerization initiator can be used. Such a polymerization initiator may be used singly, or two or more thereof may be used in combination. Further, a radical photopolymerization initiator and a photosensitizer may be used in combination as well.

Examples of the radical photopolymerization initiator include benzophenone, 2,4,6-trimethylbenzophenone, 4,4-bis(diethylamino)benzophenone, 4-phenylbenzophenone, methyl-o-benzoyl benzoate, thioxanthone, diethylthioxanthone, isopropylthioxanthone, chlorothioxanthone, 2-ethylanthraquinone, t-butylanthraquinone, diethoxyacetophenone, 2-hydroxy-2-methyl-1-phenylpropan-1-one, benzyl dimethyl ketal, 1-hydroxycyclohexyl phenyl ketone, benzoin methyl ether, benzoin ethyl ether, benzoin isopropyl ether, benzoin isobutyl ether, methylbenzoyl formate, 2-methyl-1-{4-(methylthio)phenyl)}-2-morpholinopropan-1-one, 2,6-dimethylbenzoyldiphenylphosphine oxide, 2,4,6-trimethylbenzoyldiphenylphosphine oxide, bis(2,6-dimethoxybenzoyl)-2,4,4-trimethylpentylphosphine oxide, bis(2,4,6-trimethylbenzoyl)phenylphosphine oxide, and 2-hydroxy-1-[4-[4-(2-hydroxy-2-methyl-propionyl)-benzyl]-phenyl]-2-methyl-propan-1-one.

Thereamong, from the standpoint of attaining a high curing rate and sufficiently increasing the crosslinking density, benzophenone, 2-hydroxy-2-methyl-1-phenylpropan-1-one, 1-hydroxycyclohexyl phenyl ketone, 2,4,6-trimethylbenzoyldiphenylphosphine oxide and 2-hydroxy-1-[4-[4-(2-hydroxy-2-methyl-propionyl)-benzyl]-phenyl]-2-methyl-propan-1-one are preferred, and 1-hydroxycyclohexyl phenyl ketone, 2,4,6-trimethylbenzoyldiphenylphosphine oxide and 2-hydroxy-1-[4-[4-(2-hydroxy-2-methyl-propionyl)-benzyl]-phenyl]-2-methyl-propan-1-one are more preferred.

When the active energy ray-curable polymer composition contains a compound having a cationic polymerizable group such as an epoxy group along with a radical polymerizable group, a cationic photopolymerization initiator may also be incorporated therein as a polymerization initiator along with the above-described radical photopolymerization initiator. As this cationic photopolymerization initiator, any known cationic photopolymerization initiator can be used.

In the active energy ray-curable polymer composition, the content of these polymerization initiators is preferably 10 parts by weight or less, more preferably 5 parts by weight or less, with respect to a total of 100 parts by weight of the above-described active energy ray-reactive components. When the content of the polymerization initiators is 10 parts by weight or less, a reduction in the mechanical strength caused by decomposed initiators is unlikely to occur, which is preferred.

The photosensitizer may be used for the same purpose as the polymerization initiator. The photosensitizer may be used singly, or two or more thereof may be used in combination. As the photosensitizer, any known photosensitizer can be used within a range where the effects of the present invention are obtained. Examples of such a photosensitizer include ethanolamine, diethanolamine, triethanolamine, N-methyldiethanolamine, methyl 4-dimethylaminobenzoate, ethyl 4-dimethylaminobenzoate, amyl 4-dimethylaminobenzoate, and 4-dimethylaminoacetophenone.

In the active energy ray-curable polymer composition, the content of the photosensitizer is preferably 10 parts by weight or less, more preferably 5 parts by weight or less, with respect to a total of 100 parts by weight of the above-described active energy ray-reactive components. When the content of the photosensitizer is 10 parts by weight or less, a reduction in the mechanical strength due to a decrease in the crosslinking density is unlikely to occur, which is preferred.

The above-described additive is optional, and a variety of materials that are added to a composition used for the same application can be used as the additive. Such an additive may be used singly, or two or more thereof may be used in combination. Examples of the additive include fillers, such as glass fibers, glass beads, silica, alumina, calcium carbonate, mica, zinc oxide, titanium oxide, talc, kaolin, metal oxides, metal fibers, iron, lead and metal powders; carbon materials, such as carbon fibers, carbon blacks, graphites, carbon nanotubes and fullerenes (e.g., C60) (fillers and carbon materials may be hereinafter collectively called "inorganic component"); modifiers, such as antioxidants, thermal stabilizers, ultraviolet absorbers, HALS (hindered-amine light stabilizers), anti-fingerprint agents, surface hydrophilization agents, antistatic agents, lubricity-imparting agents, plasticizers, release agents, antifoaming agents, leveling agents, precipitation inhibitors, surfactants, thixotropy-imparting agents, lubricants, flame retardants, flame retardant aids, polymerization inhibitors, bulking agents, and silane coupling agents; coloring agents, such as pigments, dyes, and hue modifiers; and curing agents, catalysts and curing accelerators, which are required for the synthesis of monomers and/or oligomers thereof or inorganic components.

In the active energy ray-curable polymer composition, the content of these additives is preferably 10 parts by weight or less, more preferably 5 parts by weight or less, with respect to a total of 100 parts by weight of the above-described active energy ray-reactive components. When the content of the additives is 10 parts by weight or less, a reduction in the mechanical strength due to a decrease in the crosslinking density is unlikely to occur, which is preferred.

The above-described solvent can be used for the purpose of adjusting the viscosity of the active energy ray-curable polymer composition in accordance with, for example, the coating method employed for forming a coating film of the active energy ray-curable polymer composition. The solvent may be used singly, or two or more thereof may be used in combination. As the solvent, any known solvent can be used within a range where the effects of the present invention are obtained. Examples of a preferred solvent include toluene, xylene, ethyl acetate, butyl acetate, isopropanol, isobutanol, cyclohexane, methyl ethyl ketone, and methyl isobutyl ketone. The solvent can be usually used in an amount of less than 200 parts by weight with respect to 100 parts by mass of solid components of the active energy ray-curable polymer composition.

A method of incorporating an optional component(s), such as the above-described additive(s), into the active energy ray-curable polymer composition is not particularly restricted, and examples thereof include conventionally known mixing and dispersion methods. In order to more certainly disperse the optional component(s), it is preferred to perform a dispersion treatment using a disperser. Specifically, a treatment method using, for example, a twin-roll mill, a triple-roll mill, a bead mill, a ball mill, a sand mill, a pebble mill, a trommel mill, a sand grinder, a Szegvari attritor, a planetary stirrer, a high-speed impeller disperser, a high-speed stone mill, a high-speed impact mill, a kneader, a homogenizer, or an ultrasonic disperser may be employed.

The viscosity of the active energy ray-curable polymer composition can be adjusted as appropriate in accordance with the intended use, the mode of use and the like of the composition; however, from the standpoints of the ease of handling, coatability, moldability, stereolithographic properties and the like, the viscosity measured by an E-type viscometer (rotor: 1034'×R24) at 25° C. is preferably 10 mPa·s or higher, more preferably 100 mPa·s or higher, but preferably 100,000 mPa·s or less, more preferably 50,000 mPa·s or less. The viscosity of the active energy ray-curable polymer composition can be adjusted by changing, for example, the content of the urethane (meth)acrylate-basedoligomer, and the types and the blending ratios of the above-described optional components.

As a method of coating the active energy ray-curable polymer composition, any known method, such as a bar coater method, an applicator method, a curtain flow coater method, a roll coater method, a spray method, a gravure coater method, a comma coater method, a reverse roll coater method, a lip coater method, a die coater method, a slot die coater method, an air knife coater method or a dip coater method, can be applied and, thereamong, a bar coater method and a gravure coater method are preferred.

<2-23. Cured Film and Laminate>

A cured film can be obtained by irradiating the active energy ray-curable polymer composition with an active energy ray.

As the active energy ray for curing the composition, for example, an infrared ray, visible light, ultraviolet ray, X-ray, electron beam, α-ray, β-ray, or γ-ray can be used. From the standpoints of the equipment cost and the productivity, it is preferred to use an electron beam or an ultraviolet ray and, as a light source, for example, an electron beam irradiation apparatus, an ultrahigh-pressure mercury lamp, a high-pressure mercury lamp, a medium-pressure mercury lamp, a low-pressure mercury lamp, a metal halide lamp, an Ar laser, a He—Cd laser, a solid-state laser, a xenon lamp, a high-frequency induction mercury lamp, or sunlight is suitable.

The irradiation dose of the active energy ray can be selected as appropriate in accordance with the type of the active energy ray and, for example, when the curing is performed by electron beam irradiation, the irradiation dose is preferably 1 to 10 Mrad. Meanwhile, when the curing is performed by ultraviolet ray irradiation, the irradiation dose is preferably 50 to 1,000 mJ/cm$^2$. The atmosphere during the curing may be the air or an inert gas such as nitrogen and argon. Further, the irradiation may be performed in a closed space between a film or glass and a metal mold.

The thickness of the cured film may be decided as appropriate in accordance with the intended use; however, the lower limit is preferably 1 μm, more preferably 3 μm, particularly preferably 5 μm, while the upper limit is preferably 200 μm, more preferably 100 μm, particularly preferably 50 μm. When the film thickness is 1 μm or greater, the design properties and functionality are favorably expressed after three-dimensional processing, whereas when the film thickness is 200 μm or less, good internal curability and three-dimensional processing suitability are attained, both of which cases are preferred. Further, for the industrial use, the lower limit of the thickness of the cured film is preferably 1 μm, while the upper limit is preferably 100 μm, more preferably 50 μm, particularly preferably 20 m, most preferably 10 μm.

A laminate can be obtained by arranging a layer composed of the above-described cured film on a substrate. This laminate is not particularly restricted as long as it has a layer composed of the cured film, and the laminate may have a layer other than the substrate and the cured film, between or outside of the substrate and the cured film. Moreover, the laminate may have a plurality of substrate and/or cured film layers.

As a method of obtaining a laminate having plural cured film layers, any known method, such as a method in which all of the layers are laminated in an uncured state and subsequently cured with an active energy ray, a method in which a lower layer is cured or semi-cured with an active energy ray and an upper layer is subsequently applied thereon, followed by curing of the resultant with an active energy ray, or a method in which layers are each applied onto a release film or a base film and these layers are subsequently pasted together in an uncured or semi-cured state, can be employed; however, from the standpoint of improving the adhesion between the layers, a method in which the layers are laminated in an uncured state and subsequently cured with an active energy ray is preferred. As a method of laminating the layers in an uncured state, any known method, examples of which include, but not limited to: sequential coating of applying a lower layer first and then overlaying an upper layer thereon, and simultaneous multi-layer coating of simultaneously applying two or more layers from multiple slits in a laminated manner, can be employed.

Examples of the substrate include articles of various shapes, for example, plates made of various plastics, such as polyesters (e.g., polyethylene terephthalate and polybutylene terephthalate), polyolefins (e.g., polypropylene and polyethylene), nylons, polycarbonates and (meth)acrylic resins, glasses, or metals.

The cured film can be a film that has excellent contamination resistance against general household contaminants, such as inks and ethanol, as well as excellent hardness, and laminates using the cured film as a coating film on various substrates can have excellent design properties and surface protection.

Further, the active energy ray-curable polymer composition is capable of yielding a cured film which satisfies such flexibility that can conform to deformation in three-dimensional processing, the elongation at break, the mechanical strength, the contamination resistance and the hardness all at the same time, taking into consideration the calculated molecular weight between network crosslinking points.

Moreover, the active energy ray-curable polymer composition is expected to enable simple production of a thin film-form resin sheet by single-layer coating.

The elongation at break of the cured film, which is a value measured for the cured film cut into a width of 10 mm by performing a tensile test using a TENSILONtensile tester (TENSILON UTM-III-100, manufactured by Orientec Co., Ltd.) under the conditions of a temperature of 23° C., a tensile rate of 50 mm/min and a chuck distance of 50 mm, is preferably not less than 50%, more preferably not less than 75%, still more preferably not less than 100%, particularly preferably not less than 120%.

The above-described cured film and laminate can be used as films alternative to paint coating, and they can be effectively applied to, for example, construction/decorative materials for interiors and exteriors, and various members of automobiles, home electronics and the like.

EXAMPLES

The present invention will now be described more concretely by way of Examples and Comparative Examples; however, the present invention is not restricted thereto within the gist of the present invention.

[Evaluation Methods]

Polycarbonate polyols and polyurethanes obtained in the below-described Examples and Comparative Examples were evaluated by the following methods.

[Evaluation of Polycarbonate Polyols]

<Quantification of Phenoxy Group Amount, Diol Content, Branched Alcohol Content, and Phenol Content>

The subject polycarbonate diol was dissolved in $CDCl_3$, and 400-MHz $^1$H-NMR spectroscopy (AL-400, manufactured by JEOL Ltd.) was performed to identify phenoxy groups, a diol(s), a branched alcohol(s) and a phenol(s) based on the signal positions of the respective components, after which the content of each component was calculated from integral values. The detection limits in this process were 100 ppm for the weight of a phenol with respect to the weight of the whole sample, and 0.1% by weight for dihydroxy compounds such as the compound represented by Formula (A) and the compound represented by Formula (B). The ratio of phenoxy groups was calculated from the ratio of between an integral value for one proton of the phenoxy group and an integral value for one proton of a whole terminal, and the detection limit for a phenoxy group was 0.05% with respect to a whole terminal.

<Content Ratio (% by weight) of Oxyalkylene Glycol (A1)>

The content ratio (% by weight) of the oxyalkylene glycol (A1) in the diol (A) was determined as follows by performing a GC analysis after hydrolysis of the subject polycarbonate polyol.

First, 0.5 g of the subject polycarbonate polyol was precisely weighed, placed in a 100-mL Erlenmeyer flask, and dissolved by adding thereto 5 mL of tetrahydrofuran. Next, 45 mL of methanol and 5 mL of a 25%-by-weight aqueous sodium hydroxide solution were added. A condenser was attached to the 100-mL Erlenmeyer flask, and hydrolysis was performed by heating the flask in a water bath at 75 to 80° C. for 30 minutes. After the resultant was allowed to cool at room temperature, sodium hydroxide was neutralized with an addition of 5 mL of 6N hydrochloric acid so as to adjust the pH to 2 to 4. The whole amount of the resultant was transferred to a 100-mL volumetric flask and, after washing the inside of the Erlenmeyer flask twice with an appropriate amount of methanol, the washings were also transferred to the 100-mL volumetric flask. An appropriate amount of methanol was added to adjust the volume to 100 mL, and the resulting solution was mixed in the volumetric flask. The supernatant was recovered, filtered through a filter, and then analyzed by gas chromatography (GC). As for the concentration of each diol contained in the diol (A), a calibration curve was prepared for a standard substance, and the concentration in % by weight was calculated from the area ratio obtained by the GC analysis.

<Molar Ratio of Structural Unit Derived from Oxyalkylene Glycol (A1) and Structural Units Derived from Branched Alcohol (B)>

The subject polycarbonate diol was dissolved in $CDCl_3$, and 400-MHz $^1$H-NMR spectroscopy (AL-400, manufactured by JEOL Ltd.) was performed to determine the molar ratios of a structural unit derived from the oxyalkylene glycol (A1) and structural units derived from the branched alcohol (B) based on the signal positions of the respective components. In addition, the molar ratios of a terminal derived from the oxyalkylene glycol (A1) and a terminal derived from the branched alcohol (B) were also determined in the same manner.

<Ratio of Structural Unit (X1)>

The ratio of the structural unit (X1) in the structural units derived from the branched alcohol (B) was calculated from the ratio of integral values obtained by the $^1$H-NMR spectroscopy (the ratio (% by mole) of the structural unit (X1) in the structural units derived from the branched alcohol (B) is hereinafter referred to as "structural unit (X1) content ratio").

For example, when the branched alcohol (B) was trimethylolpropane, this ratio was determined as follows, and the same analysis based on $^1$H-NMR can be applied to other branched alcohols.

The subject polycarbonate diol was dissolved in $CDCl_3$, and 400-MHz $^1$H-NMR spectroscopy (AL-400, manufactured by JEOL Ltd.) was performed to determine the ratios of the respective structural units from the below-described chemical shift values (δ) and integrated values thereof. It is noted here that, since the chemical shift values may slightly vary depending on the formulation, the way of acquiring the integral values is modified as appropriate in such a case.

Integral value for δ0.91 to 1.01 ppm=a (representing the structural unit (X1))

Integral value for δ0.82 to 0.90 ppm=b (representing a structural unit(s) other than the structural unit (X1))

Structural unit (X1) content ratio (% by mole)=a/(a+b)×100

<Hydroxyl Value>

The hydroxyl value of each polycarbonate polyol was measured by a method using an acetylation reagent in accordance with JIS K1557-1.

[Evaluation of Polyurethanes]

<Solvent Resistance>

A polyurethane solution was applied onto a fluorocarbon resin sheet (fluorine tape NITOFLON 900, thickness=0.1 mm, manufactured by Nitto Denko Corporation) using a 9.5-mil applicator and sequentially dried under the conditions of at 50° C. for 5 hours, at 100° C. for 0.5 hours, at 100° C. for 0.5 hours in vacuum, and then at 80° C. for 15 hours. Test pieces of 3 cm×3 cm were cut out from the thus obtained polyurethane film and then placed in glass dishes of 10 cmφ in diameter containing 50 mL of the respective test solvents. For each test solvent, the weight of the test piece was measured after immersion at the below-described temperature for the below-described time, and the rate of change (%) in the weight of the test piece before and after the immersion (=(Weight of test piece after immersion−Weight of test piece before immersion)/Weight of test piece before immersion×100) was calculated. It is noted here that a weight change rate closer to 0% indicates superior oleic acid resistance.

Oleic acid resistance: the test piece was immersed in oleic acid at 80° C. for 16 hours.

Ethyl acetate resistance: the test piece was immersed in ethyl acetate at room temperature for 20 minutes.

Ethanol resistance: the test piece was immersed in ethanol at room temperature for 1 hour.

<Tensile Test at Room Temperature>

In accordance with JIS K6301, for a polyurethane test piece in the form of a strip having a width of 10 mm, a length of 100 mm and a thickness of about 50 μm, a tensile test was performed using a tensile tester [trade name: "TENSILON UTM-III-100", manufactured by Orientec Co., Ltd.] at a chuck distance of 50 mm, a tensile rate of 500 mm/min and a temperature of 23° C. (relative humidity: 55%) to measure the stress required for the test piece to be broken at each elongation value. The stress measured at 100% elongation and the stress measured at 300% elongation were defined as "100% modulus (100% M)" and "300% modulus (300% M)", respectively.

[Raw Materials Used]

The raw materials used for the production of polycarbonate polyols and polyurethanes were as follows.

Diethylene glycol (hereinafter, may be abbreviated as "DEG"): manufactured by Mitsubishi Chemical Corporation Triethylene glycol (hereinafter, may be abbreviated as "TEG"): manufactured by Mitsubishi Chemical Corporation Trimethylolpropane (hereinafter, may be abbreviated as "TMP"): manufactured by Mitsubishi Gas Chemical Company, Inc.

Diphenyl carbonate (hereinafter, may be abbreviated as "DPC"): manufactured by Mitsubishi Chemical Corporation Magnesium acetate tetrahydrate: manufactured by Wako Pure Chemical Industries, Ltd.

1,4-butanediol: manufactured by Mitsubishi Chemical Corporation

Diphenylmethane diisocyanate (hereinafter, may be abbreviated as "MDI"): manufactured by Nippon Polyurethane Industry Co., Ltd.

Urethanization catalyst NEOSTANN U-830: manufactured by Nitto Kasei Co., Ltd.

Dehydrated N,N-dimethylformamide: manufactured by Wako Pure Chemical Industries, Ltd.

Production of Polycarbonate Polyols and Evaluation I

Example I-1

To a 5-L glass separable flask equipped with a stirrer, a distillate trap and a pressure adjusting device, 786.1 g of diethylene glycol (DEG), 744.7 g of triethylene glycol (TEG), 25.5 g of trimethylolpropane (TMP), 2,525.0 g of diphenyl carbonate (DPC) and 6.3 mL of an aqueous magnesium acetate tetrahydrate solution (concentration: 8.4 g/L, magnesium acetate tetrahydrate: 53 mg) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 2 hours while removing phenol and unreacted dihydroxy compounds out of the system, whereby a polycarbonate diol-containing composition was produced. Thereafter, the catalyst was deactivated with an addition of 1.35 mL of a 0.85% aqueous phosphoric acid solution to obtain a polycarbonate polyol-containing composition.

The thus obtained polycarbonate polyol-containing composition was transferred to a thin-film distillation apparatus at a flow rate of 20 g/min, and thin-film distillation (temperature: 200° C., pressure: 53 to 67 Pa) was performed. As the thin-film distillation apparatus, a molecular distillation apparatus Model MS-300 manufactured by Sibata Scientific Technology Ltd., which was equipped with an internal condenser having a diameter of 50 mm, a height of 200 mm and an area of 0.0314 m² and a jacket, was used.

The results of evaluating the characters and physical properties of the polycarbonate polyol obtained by this thin-film distillation are shown in Table 1.

Example I-2

To a 1-L glass separable flask equipped with a stirrer, a distillate trap and a pressure adjusting device, 231.8 g of diethylene glycol (DEG), 219.6 g of triethylene glycol (TEG), 7.5 g of trimethylolpropane (TMP), 741.2 g of diphenyl carbonate (DPC) and 1.9 mL of an aqueous magnesium acetate tetrahydrate solution (concentration: 8.4 g/L) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 15 hours while removing phenol and unreacted dihydroxy compounds out of the system. Thereafter, the catalyst was deactivated with an addition of 0.45 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Example I-3

To a 5-L glass separable flask equipped with a stirrer, a distillate trap and a pressure adjusting device, 786.1 g of diethylene glycol (DEG), 741.6 g of triethylene glycol (TEG), 0.83 g of trimethylolpropane (TMP), 2,471.5 g of diphenyl carbonate (DPC) and 6.3 mL of an aqueous magnesium acetate tetrahydrate solution (concentration: 8.4 g/L, magnesium acetate tetrahydrate: 53 mg) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 2 hours while removing phenol and unreacted dihydroxy compounds out of the system. Thereafter, the catalyst was deactivated with an addition of 1.35 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Example I-4

To a 5-L glass separable flask equipped with a stirrer, a distillate trap and a pressure adjusting device, 787.7 g of diethylene glycol (DEG), 724.3 g of triethylene glycol (TEG), 33.0 g of trimethylolpropane (TMP), 2,475.0 g of diphenyl carbonate (DPC) and 6.3 mL of an aqueous magnesium acetate tetrahydrate solution (concentration: 8.4 g/L, magnesium acetate tetrahydrate: 53 mg) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 7 hours while removing phenol and unreacted dihydroxy compounds out of the system. Thereafter, the catalyst was deactivated with an addition of 1.35 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Example I-5

To a 5-L glass separable flask equipped with a stirrer, a distillate trap and a pressure adjusting device, 756.7 g of diethylene glycol (DEG), 705.3 g of triethylene glycol (TEG), 54.2 g of trimethylolpropane (TMP), 2,483.9 g of diphenyl carbonate (DPC) and 6.2 mL of an aqueous magnesium acetate tetrahydrate solution (concentration: 8.4 g/L, magnesium acetate tetrahydrate: 52 mg) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 9 hours while removing phenol and unreacted dihydroxy compounds out of the system. Thereafter, the catalyst was deactivated with an addition of 1.3 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Comparative Example I-1

To a 1-L glass separable flask equipped with a stirrer, a distillate trap and a pressure adjusting device, 237.0 g of diethylene glycol (DEG), 223.6 g of triethylene glycol (TEG), 739.5 g of diphenyl carbonate (DPC) and 1.9 mL of an aqueous magnesium acetate tetrahydrate solution (concentration: 8.4 g/L) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 5 hours while removing phenol and unreacted dihydroxy compounds out of the system. Thereafter, the catalyst was deactivated with an addition of 0.45 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Comparative Example I-2

To a 1-L glass separable flask equipped with a stirrer, a distillate trap and a pressure adjusting device, 211.4 g of diethylene glycol (DEG), 200.2 g of triethylene glycol (TEG), 6.8 g of trimethylolpropane (TMP), 690.6 g of diphenyl carbonate (DPC) and 1.7 mL of an aqueous magnesium acetate tetrahydrate solution (concentration: 8.4 g/L) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 20 minutes while removing phenol and unreacted dihydroxy compounds out of the system. Thereafter, the catalyst was deactivated with an addition of 0.45 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Comparative Example I-3

To a 1-L glass separable flask equipped with a stirrer, a distillate trap and a pressure adjusting device, 204.0 g of diethylene glycol (DEG), 189.9 g of triethylene glycol (TEG), 24.9 g of trimethylolpropane (TMP), 681.2 g of diphenyl carbonate (DPC) and 1.7 mL of an aqueous magnesium acetate tetrahydrate solution (concentration: 8.4 g/L) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 5 hours while removing phenol and unreacted dihydroxy compounds out of the system. Thereafter, the catalyst was deactivated with an addition of 0.45 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

Comparative Example I-4

To a 5-L glass separable flask equipped with a stirrer, a distillate trap and a pressure adjusting device, 753.0 g of diethylene glycol (DEG) as the oxyalkylene diol (A1), 462.2 g of 1,6-hexanediol (16HD) as a diol other than the oxyalkylene diol (A1), 22.5 g of trimethylolpropane (TMP), 2,262.3 g of diphenyl carbonate (DPC) and 5.7 mL of an aqueous magnesium acetate tetrahydrate solution (concentration: 8.4 g/L, magnesium acetate tetrahydrate: 48 mg) were added, followed by purging with nitrogen gas. The contents were heat-dissolved by raising the internal temperature to 160° C. with stirring. Subsequently, after the pressure was reduced to 24 kPa over a period of 2 minutes, the reaction was allowed to proceed for 90 minutes while removing phenol out of the system. Then, the reaction was continued while reducing the pressure to 9.3 kPa over a period of 90 minutes and further to 0.7 kPa over a period of 30 minutes, after which the temperature was raised to 170° C. and the reaction was allowed to proceed for another 5 hours while removing phenol and unreacted dihydroxy compounds out of the system. Thereafter, the catalyst was deactivated with an addition of 1.1 mL of a 0.85% aqueous phosphoric acid solution to obtain a polycarbonate polyol-containing composition. Then, thin-film distillation was performed in the same manner as in Example I-1, and the results of evaluating the characters and physical properties of the thus obtained polycarbonate polyol are shown in Table 1.

TABLE 1

|  | Content ratio of (A1) in diol (A) (% by weight) | | Content ratio of diol other than (A1) in diol (A) (% by weight) | Content ratio of branched alcohol (B) (% by mole) | Content ratio of structural unit (X1) (% by mole) | Hydroxyl value of PCP (mg – KOH/g) |
|---|---|---|---|---|---|---|
|  | DEG | TEG | 16HD | TMP | | |
| Example I-1 | 51.2 | 48.8 |  | 1.5 | 43 | 42.5 |
| Example I-2 | 50.8 | 49.2 |  | 1.5 | 16 | 44.5 |

TABLE 1-continued

|  | Content ratio of (A1) in diol (A) (% by weight) | | Content ratio of diol other than (A1) in diol (A) (% by weight) | Content ratio of branched alcohol (B) (% by mole) | Content ratio of structural unit (X1) (% by mole) | Hydroxyl value of PCP (mg – KOH/g) |
|---|---|---|---|---|---|---|
|  | DEG | TEG | 16HD | TMP | | |
| Example I-3 | 52.4 | 47.6 | | 0.05 | 26 | 42.5 |
| Example I-4 | 51.6 | 48.4 | | 2.0 | 32 | 44.1 |
| Example I-5 | 51.8 | 48.2 | | 3.2 | 24 | 42.6 |
| Comparative Example I-1 | 51.1 | 48.9 | | 0 | | 47.7 |
| Comparative Example I-2 | 51.4 | 48.6 | | 1.5 | 52 | 44.6 |
| Comparative Example I-3 | 51.8 | 48.2 | | 5.5 | 32 | 44.5 |
| Comparative Example I-4 | 62 | 0 | 38 | 1.5 | 23 | 35.2 |

Production of Polyurethanes and Evaluation II

Examples II-1 to 5 and Comparative Examples II-1 to 4

To a separable flask provided with a thermocouple and a stirrer, 81.42 g of a polycarbonate polyol which had been heated to 80° C., 2.77 g of 1,4-butanediol, 232.18 g of dehydrated N,N-dimethylformamide and 22.2 mg of a urethanization catalyst (NEOSTANN U-830) were added, and the separable flask was immersed in an oil bath set at 55° C. The added materials were stirred at 60 rpm for about 1 hour while heating the inside of the separable flask under a nitrogen atmosphere. Once the polycarbonate polyol was dissolved in the solvent, diphenylmethane diisocyanate (MDI) was added thereto in small amounts. Starting 10 minutes after the increase in the internal temperature due to the heat of reaction stopped and the temperature started to decrease, MDI was further added in small amounts. The further addition of MDI was repeated to add a total of 15.02 g of MDI eventually, whereby a polyurethane solution was obtained. From the thus obtained polyurethane solution, a test film was prepared by the above-described method, and the physical properties thereof were evaluated. The results obtained by the same method in Examples II-1 to 5 and Comparative Examples II-1 to 4 are shown in Table 2. Table 2 also shows the values of NCO/OH, which is the equivalent ratio of all isocyanate groups and hydroxy groups that were used. It is noted here that, in Comparative Example II-3, a polyurethane solution could not be produced due to the occurrence of gelation during the polyurethane production.

As the polycarbonate polyol, the polycarbonate polyol produced in Example I-1 was used in Example II-1; the polycarbonate polyol produced in Example I-2 was used in Example II-2; the polycarbonate polyol produced in Example I-3 was used in Example II-3; the polycarbonate polyol produced in Example I-4 was used in Example II-4; the polycarbonate polyol produced in Example I-5 was used in Example II-5; the polycarbonate polyol produced in Comparative Example I-1 was used in Comparative Example II-1; the polycarbonate polyol produced in Comparative Example I-2 was used in Comparative Example II-2; the polycarbonate polyol produced in Comparative Example I-3 was used in Comparative Example II-3; and the polycarbonate polyol produced in Comparative Example I-4 was used in Comparative Example II-4.

TABLE 2

|  | NCO/OH molar ratio | Solvent resistance (weight increase rate (%)) | | | Tensile test at room temperature | | | |
|---|---|---|---|---|---|---|---|---|
|  | | Oleic acid | Ethyl acetate | Ethanol | 100% M (MPa) | 300% M (MPa) | Elongation at break % | Breaking strength (MPa) |
| Example II-1 | 0.9 | 2.4 | 39.9 | 5.4 | 1.3 | 2.1 | 1,023 | 4.6 |
| Example II-2 | 0.9 | 1.2 | 32.5 | 5.3 | 1.3 | 2.4 | 993 | 4.2 |
| Example II-3 | 0.9 | 0.9 | 40.9 | 7.1 | 1.5 | 2.0 | 1,202 | 6.9 |
| Example II-4 | 0.9 | 1.1 | 25.8 | 6.7 | 1.3 | 2.3 | 960 | 4.3 |

TABLE 2-continued

| | NCO/OH molar ratio | Solvent resistance (weight increase rate (%)) | | | Tensile test at room temperature | | | |
|---|---|---|---|---|---|---|---|---|
| | | Oleic acid | Ethyl acetate | Ethanol | 100% M (MPa) | 300% M (MPa) | Elongation at break % | Breaking strength (MPa) |
| Example II-5 | 0.9 | 2.3 | 48.1 | 7.4 | 0.8 | 1.6 | 1,000 | 3.2 |
| Comparative Example II-1 | 0.9 | 26.0 | 40.5 | 21.7 | 0.6 | — | 101 | 0.6 |
| Comparative Example II-2 | 1.0 | 1.3 | 44.6 | 5.8 | 1.0 | 1.7 | 316 | 1.7 |
| Comparative Example II-3 | 0.9 | A polyurethane soloution could not be produced due to gelation | | | | | | |
| Comparative Example II-4 | 0.9 | 8.2 | dissolved | 10.4 | 0.7 | 1.0 | 961 | 1.8 |

<Discussion>

From the above results, the followings are seen.

As described above, as a polyurethane, a smaller value of weight change rate is more preferred since such a polyurethane has a higher solvent resistance.

In addition, as a polyurethane, smaller values of 100% M, 300% M and breaking strength are more preferred since such a polyurethane has a higher flexibility. Moreover, as a polyurethane, a higher elongation at break is more preferred since such a polyurethane has a higher mechanical strength.

In the solvent resistance tests for oleic acid, ethyl acetate and ethanol, the polyurethane of Comparative Example II-1, which used a polycarbonate polyol that was produced without using TMP as a polyhydric alcohol raw material, exhibited a high weight increase rate and had a low solvent resistance.

In addition, the polyurethane of Comparative Example II-1 exhibited a low elongation at break and a low breaking strength, and thus had a low mechanical strength.

On the other hand, the polyurethanes of Examples II-1 to 5, which were each produced from a polycarbonate polyol having a specific ratio of the cyclic structural unit (X1) with the use of a specific amount of TMP as a polyhydric alcohol raw material, exhibited a low weight change rate in the solvent resistance tests and thus had excellent solvent resistance. Moreover, it is apparent that these polyurethanes not only exhibited low 100% M, 300% M and breaking strength and thus had excellent flexibility, but also showed a high elongation at break and thus had excellent mechanical strength.

Comparing the solvent resistance between Examples II-1 and 2 and Comparative Example II-2, it is seen that the polyurethanes of Examples II-1 and 2, in which a polycarbonate polyol having a low content ratio of the structural unit (X1) was used, had a higher solvent resistance in ethyl acetate. In addition, it is apparent that the polyurethanes of Examples II-1 and 2 also had superior mechanical strength since they had a higher elongation at break.

In Comparative Example II-3, since the content ratio of the branched alcohol (B) in the polycarbonate polyol was high and a large amount of crosslinked structures was generated during the polyurethane production, gelation occurred in the polyurethane solution.

Comparing Examples II-1 and 2 with Comparative Example II-4, it is seen that the polyurethane of Comparative Example II-4, in which the content ratio of the oxyalkylene glycol (A1) in the diol (A) was low, had a lower solvent resistance since it exhibited higher weight increase rates in the solvent resistance tests with oleic acid and ethanol and was dissolved in the solvent resistance test with ethyl acetate.

What is claimed is:

1. A polycarbonate polyol comprising structural units derived from a polyhydric alcohol and having a hydroxyl value of 20 mg KOH/g to 450 mg KOH/g, wherein
the polycarbonate polyol is produced by a transesterification reaction of the polyhydric alcohol with a carbonate compound,
the polyhydric alcohol comprises a diol (A) and a trihydric to hexahydric branched alcohol (B), comprising a partial structure (B2) represented by the following Formula (B2), having 4 to 12 carbon atoms,
the diol (A) comprises an oxyalkylene glycol (A1) represented by the following Formula (A1) in an amount of 70% by weight or higher based on total weight of diol (A),
a ratio of structural units derived from the branched alcohol (B) is 0.005% by mole to 5.0% by mole with respect to a total amount of the structural units derived from the polyhydric alcohol, and
a ratio of a structural unit (X2) represented by the following Formula (X2) in the structural units derived from the branched alcohol (B) is not higher than 50% by mole based on the total moles of structural units derived from the branched alcohol (B):

(A1)

wherein, m represents an integer of 2 to 4; $R^{41}$ represents a carbon chain optionally containing a branch having 2 to 5 carbon atoms; and m $R^{41}$s contained in Formula (A1) are the same or different

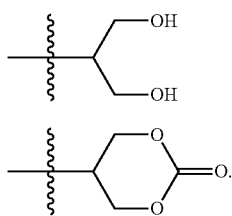

2. The polycarbonate polyol according to claim 1, wherein the branched alcohol (B) is a trihydric alcohol.

3. The polycarbonate polyol according to claim 2, wherein the trihydric alcohol is trimethylolpropane.

4. The polycarbonate polyol according to claim 1, wherein the oxyalkylene glycol (A1) comprises at least one selected from the group consisting of diethylene glycol, triethylene glycol, tetraethylene glycol, and dipropylene glycol.

5. The polycarbonate polyol according to claim 4, wherein the oxyalkylene glycol (A1) comprises diethylene glycol and/or triethylene glycol.

6. The polycarbonate polyol according to claim 5, wherein a total content ratio of diethylene glycol and triethylene glycol in the diol (A) is not less than 70% by weight.

7. The polycarbonate polyol according to claim 5, wherein a weight ratio of diethylene glycol and triethylene glycol in the oxyalkylene glycol (A1) is 10:90 to 90:10 (diethylene glycol:triethylene glycol).

8. A polyurethane obtainable by reacting the polycarbonate polyol according to claim 1 with a compound comprising isocyanate groups.

9. A polyurethane, obtainable by reacting a polycarbonate polyol with a compound comprising isocyanate groups, wherein
the polycarbonate polyol comprises structural units derived from a polyhydric alcohol and has a hydroxyl value of 20 mg KOH/g to 450 mg KOH/g,
the polycarbonate polyol is produced by a transesterification reaction of the polyhydric alcohol with a carbonate compound,
the polyhydric alcohol comprises a diol (A) and a trihydric to hexahydric branched alcohol (B), comprising a partial structure (B2) represented by the following Formula (B2), having 4 to 12 carbon atoms,
the diol (A1) comprises an oxyalkylene glycol (A1) represented by the following Formula (A1) and a content ratio of the oxyalkylene glycol (A1) in the diol (A) is 70% by weight or higher,
a ratio of structural units derived from the branched alcohol (B) in the polycarbonate polyol is 0.005% by mole to 5.0% by mole, the ratio being with respect to a total amount of the structural units derived from the polyhydric alcohol in the polycarbonate polyol, and
a ratio of a structural unit (X2) represented by the following Formula (X2) in the structural units derived from the branched alcohol (B) is not higher than 50% by mole based on the total moles of structural units derived from the branched alcohol (B:

wherein, in represents an integer of 2 to 4; $R^{41}$ represents a carbon chain optionally containing a branch having 2 to 5 carbon atoms; and in $R^{41}$s contained in Formula (A1) are the same or different

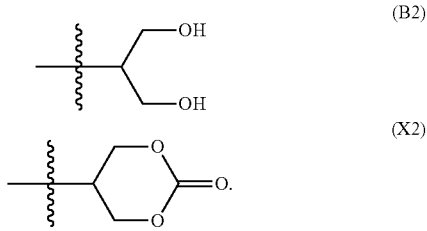

10. The polyurethane according to claim 9, which is obtainable by reacting the polycarbonate polyol, an organic polyisocyanate compound, and a chain extender.

* * * * *